United States Patent
Gauvry et al.

(10) Patent No.: US 10,047,040 B2
(45) Date of Patent: Aug. 14, 2018

(54) SULFONYLAMINOBENZAMIDE COMPOUNDS AS ANTHELMINTICS

(71) Applicant: Elanco Tiergesundheit AG, Indianapolis, IN (US)

(72) Inventors: Noelle Gauvry, Kembs (FR); Chouaib Tahtaoui, Rixheim (FR)

(73) Assignee: Elanco Tiergesundheit AG, Basel (CH)

( * ) Notice: Subject to any disclaimer, the term of this patent is extended or adjusted under 35 U.S.C. 154(b) by 0 days.

(21) Appl. No.: 15/502,512

(22) PCT Filed: Aug. 27, 2015

(86) PCT No.: PCT/US2015/047214
§ 371 (c)(1),
(2) Date: Feb. 8, 2017

(87) PCT Pub. No.: WO2016/033341
PCT Pub. Date: Mar. 3, 2016

(65) Prior Publication Data
US 2017/0226053 A1 Aug. 10, 2017

(30) Foreign Application Priority Data
Aug. 29, 2014 (EP) .................... 14182960

(51) Int. Cl.
| | | |
|---|---|---|
| C07C 311/08 | (2006.01) |
| C07F 7/08 | (2006.01) |
| C07F 5/02 | (2006.01) |
| C07D 295/155 | (2006.01) |
| C07D 333/24 | (2006.01) |
| C07D 231/12 | (2006.01) |
| C07D 213/61 | (2006.01) |
| C07D 231/56 | (2006.01) |
| C07D 213/56 | (2006.01) |
| C07D 239/30 | (2006.01) |
| C07D 239/26 | (2006.01) |
| C07D 277/30 | (2006.01) |
| C07D 213/84 | (2006.01) |
| C07D 333/28 | (2006.01) |
| C07C 311/21 | (2006.01) |
| C07C 311/14 | (2006.01) |
| C07D 309/06 | (2006.01) |
| C07D 249/08 | (2006.01) |
| C07D 277/64 | (2006.01) |

(Continued)

(52) U.S. Cl.
CPC .......... *C07C 311/08* (2013.01); *C07C 311/14* (2013.01); *C07C 311/21* (2013.01); *C07D 209/08* (2013.01); *C07D 213/56* (2013.01); *C07D 213/61* (2013.01); *C07D 213/84* (2013.01); *C07D 215/06* (2013.01); *C07D 231/12* (2013.01); *C07D 231/56* (2013.01); *C07D 237/26* (2013.01); *C07D 239/26* (2013.01); *C07D 239/30* (2013.01); *C07D 249/08* (2013.01); *C07D 263/50* (2013.01); *C07D 275/03* (2013.01); *C07D 277/30* (2013.01); *C07D 277/46* (2013.01); *C07D 277/54* (2013.01); *C07D 277/56* (2013.01); *C07D 277/60* (2013.01); *C07D 277/64* (2013.01); *C07D 285/135* (2013.01); *C07D 295/155* (2013.01); *C07D 309/06* (2013.01); *C07D 317/66* (2013.01); *C07D 333/24* (2013.01); *C07D 333/28* (2013.01); *C07D 333/78* (2013.01); *C07D 487/04* (2013.01); *C07F 5/025* (2013.01); *C07F 7/0818* (2013.01); *C07C 2601/02* (2017.05); *C07C 2601/14* (2017.05); *C07C 2602/08* (2017.05); *C07C 2602/42* (2017.05)

(58) Field of Classification Search
CPC .................. C07C 311/08; C07D 213/56
See application file for complete search history.

(56) References Cited

U.S. PATENT DOCUMENTS

| 5,077,300 A | 12/1991 | Maienfisch et al. |
| 5,132,314 A | 7/1992 | Maienfisch et al. |

(Continued)

FOREIGN PATENT DOCUMENTS

| DE | 3523705 A1 | 1/1987 |
| EP | 0420804 A2 | 4/1991 |

(Continued)

OTHER PUBLICATIONS

Fisher et al (2005): STN International, HCAPLUS database (Columbus, Ohio), Accession No. 2005: 1004700.*

(Continued)

*Primary Examiner* — Golam M Shameem
(74) *Attorney, Agent, or Firm* — Joseph Matthew Pletcher

(57) ABSTRACT

The present invention relates to a new compound of formula (I) wherein the variables have the meaning as indicated in the claims; or an enantiomer or salt thereof. The compounds of formula (I) are useful in the control of parasites, in particular endoparasites, in and on vertebrates.

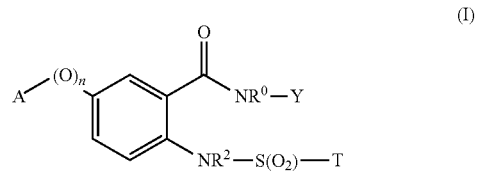

15 Claims, No Drawings

(51) Int. Cl.

| | |
|---|---|
| C07D 277/60 | (2006.01) |
| C07D 277/56 | (2006.01) |
| C07D 285/135 | (2006.01) |
| C07D 333/78 | (2006.01) |
| C07D 277/46 | (2006.01) |
| C07D 277/54 | (2006.01) |
| C07D 263/50 | (2006.01) |
| C07D 275/03 | (2006.01) |
| C07D 317/66 | (2006.01) |
| C07D 209/08 | (2006.01) |
| C07D 215/06 | (2006.01) |
| C07D 487/04 | (2006.01) |
| C07D 237/26 | (2006.01) |

(56) References Cited

U.S. PATENT DOCUMENTS

| | | | | |
|---|---|---|---|---|
| 6,458,845 | B1* | 10/2002 | Weinstock | A61K 31/18 514/604 |
| 8,518,998 | B2* | 8/2013 | Rudolphi | A61K 31/18 514/601 |
| 9,714,219 | B2* | 7/2017 | Gauvry | C07C 311/08 |

FOREIGN PATENT DOCUMENTS

| | | |
|---|---|---|
| EP | 0420805 A2 | 4/1991 |
| JP | S62-10057 A | 1/1987 |
| SU | 1685935 A1 | 10/1991 |
| SU | 1685937 A1 | 10/1991 |
| SU | 1754712 A1 | 8/1992 |
| WO | 1989/06233 A1 | 7/1989 |
| WO | 2000/02851 A1 | 6/1999 |
| WO | 2003/026415 A2 | 9/2002 |
| WO | 2005/085188 A1 | 9/2005 |
| WO | 2009/043495 A1 | 4/2009 |
| WO | 2016/016316 A1 | 2/2016 |

OTHER PUBLICATIONS

Weinstock et al (2000): STN International, HCAPLUS database (Columbus, Ohio), Accession No. 2000: 911023.*

Ming Shang, et al: "Cu(II)-Mediated C—H Amidation and Amination of Arenes: Exceptional Compatibility with Heterocycles" *Journal of the American Chemical Society* 2014 136 (9), 3354-3357.

Database CA [Online] Chemical Abstracts Service, Columbus, Ohio, US; Mikhajlitsyn, Feliks S. et al: "N-(3-nitro-4-chlorophenylsulfonyl)anthranilic acid as an intermediate for the synthesis of N-(4-chloropheny)-2-[(3-nitro-4-chlorophenylsulfonyl)amino]-5-bromobenzamide, showing antitrichocephaliasis activity", Database accession No. 1993:516978.

Database CA [Online] Chemical Abstracts Service, Columbus, Ohio, US; Mikhailitsyn, F.S. et al: "2-[(7-Bromobenzo-2,1,3-thiadiazole-4-sulfonyl)amino]-5-chlorobenzoic acid as an intermediate for an anthelmintic", Database accession No. 1992:235640.

Database CA [Online] Chemical Abstracts Service, Columbus, Ohio, US; Mikhailitsyn, F.S. et al: "2-[(Benzo-2,1,3-thiadiazole-4-sulfonyl)amino]benzoic acids as synthetic intermediates for anthelmintics", Database accession No. 1992:194327.

CAS Registry No. 1279661-65-2; STN Entry Date Apr. 13, 2011.
CAS Registry No. 1288298-00-9; STN Entry Date May 1, 2011.
CAS Registry No. 1288890-51-6; STN Entry Date May 2, 2011.
CAS Registry No. 1298896-65-7; STN Entry Date May 22, 2011.
CAS Registry No. 1333676-76-8; STN Entry Date Sep. 29, 2011.
CAS Registry No. 1390315-65-7; STN Entry Date Aug. 13, 2012.
CAS Registry No. 1445115-20-7; STN Entry Date Jul. 17, 2013.
CAS Registry No. 1572906-97-8; STN Entry Date Mar. 24, 2014.
CAS Registry No. 1590584-85-2; STN Entry Date Apr. 25, 2014.
CAS Registry No. 1606770-06-2; STN Entry Date May 19, 2014.

* cited by examiner

SULFONYLAMINOBENZAMIDE COMPOUNDS AS ANTHELMINTICS

The present invention relates to novel sulfonylaminobenzamide compounds and their use in the control of endoparasites, for example heartworms, in warm-blooded animals.

Heartworm (*Dirofilaria immitis*) is a parasitic roundworm that is spread from host to host through the bites of mosquitoes. The definite host is the dog but it can also infect cats and other warm-blooded animals. Although commonly being called "heartworm" the adult worms actually reside in the pulmonary arterial system (lung arteries) for the most part, and the primary effect on the health of the animal is damage to the lung vessels and tissue. Occasionally, adult heartworms migrate to the right heart and even the great veins in heavy infections. Heartworm infection may result in serious disease for the host.

Heartworm infections may be combatted with arsenic-based compounds; the treatment is time-consuming, cumbersome and often only partly successful. Accordingly, the main focus is on the prevention of heartworm infections. Heartworm prevention is currently performed exclusively by year round periodical administration of a macrocyclic lactone such as ivermectin, moxidectin or milbemycin oxime to the dog, cat or else warm-blooded animal. Unfortunately, upcoming resistancy of *Dirofilaria immitis* against macrocyclic lactones has been observed in certain parts of the USA. Accordingly, there is a strong need for finding new classes of compounds which are effectively controlling heartworm infections either by way of prophylaxis or by direct killing of the different stages of heartworms. It now has been found surprisingly that a group of novel sulfonylaminobenzamide compounds effectively controls endoparasites including heartworms effectively on warm-blooded animals.

SUMMARY OF THE INVENTION

The present invention therefore according to one embodiment concerns a compound of formula

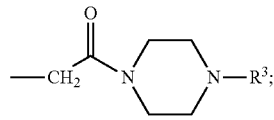

(I)

or a salt or an enantiomer thereof, wherein n is 0 or 1;

A is $C_1$-$C_6$-alkyl; $C_1$-$C_6$-haloalkyl; $C_3$-$C_6$-cycloalkyl; $C_3$-$C_6$-halocycloalkyl; 5- or 6-membered heterocycloalkyl having from 1 to 3 same or different heteroatoms selected from the group consisting of B, N, O and S, which is further unsubstituted or substituted by halogen, $C_1$-$C_4$-alkyl or $C_1$-$C_4$-alkoxy; or is phenyl which is unsubstituted or substituted by halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkyl-sulfinyl, $C_1$-$C_6$-haloalkylsulfinyl, $C_1$-$C_6$-alkylsulfonyl, $C_1$-$C_6$-haloalkylsulfonyl, $SF_5$; amino, N-mono- or N,N-di-$C_1$-$C_6$-alkylamino, tri-$C_1$-$C_4$-alkylsilyl, $C_1$-$C_6$-alkoxycarbonyl, aminocarbonyl, N-mono- or N,N-di-$C_1$-$C_6$-alkylaminocarbonyl, aminosulfonyl, N-mono- or N,N-di-$C_1$-$C_6$-alkylaminosulfonyl, $C_1$-$C_6$-alkoxycarbonylamino, N—$C_1$-$C_4$-alkyl-N—$C_1$-$C_6$-alkoxycarbonylamino, cyano, nitro, or unsubstituted or halogen-, $C_1$-$C_4$-alkyl-, $C_1$-$C_4$-haloalkyl-, $C_1$-$C_4$-alkoxy-, $C_1$-$C_4$-haloalkoxy-, amino-, cyano- or nitro-substituted $C_3$-$C_6$-heterocyclyl; or is cinnamyl, which is unsubstituted or substituted in the phenyl moiety by halogen, $C_1$-$C_4$-alkyl or $C_1$-$C_4$-alkoxy; or is a heteroaromatic radical, which is further unsubstituted or substituted by halogen, cyano, $C_1$-$C_4$-alkyl, $C_1$-$C_4$-haloalkyl, $C_1$-$C_4$-alkoxy, $C_1$-$C_4$-haloalkoxy, $C_2$-$C_4$-alkanoyl, 5- or 6-membered heterocycloalkyl-$C_1$-$C_2$-alkyl or unsubstituted or halogen-, $C_1$-$C_4$-alkyl- or $C_1$-$C_4$-alkoxy-substituted phenyl; or is a hetero-bicyclic ring radical comprising a total of 8 to 10 ring members, from which 1 to 5, preferably 1 or 2, members are same or different heteroatoms selected from the group consisting of B, N, O and S, and from which 0 to 2 members are a group C(O)—, which bicyclic ring radical is further unsubstituted or substituted by halogen, cyano, hydroxyl, $C_1$-$C_4$-alkyl or $C_1$-$C_4$-haloalkyl;

$R^2$ is H or —S($O_2$)-T;

T is $C_1$-$C_6$-alkyl, which is unsubstituted or substituted by halogen, trimethylsilyl, $C_3$-$C_6$-cycloalkyl, carboxyl or $C_1$-$C_4$-alkoxycarbonyl; $C_3$-$C_6$-cycloalkyl; $C_6$-$C_{12}$-bicarbocyclyl; phenyl which is unsubstituted or substituted by halogen, cyano, nitro, $C_1$-$C_4$-alkyl, $C_1$-$C_4$-haloalkyl or $C_1$-$C_4$-alkoxy; a 5- or 6 membered heteroaromatic radical, which is further unsubstituted or substituted by halogen, cyano, nitro, $C_1$-$C_4$-alkyl, $C_1$-$C_4$-haloalkyl or $C_1$-$C_4$-alkoxy; 5- or 6-membered heterocycloalkyl having from 1 to 3 same or different heteroatoms selected from the group consisting of N, O, S and S($O_2$), which is further unsubstituted or substituted by $C_1$-$C_4$-alkyl, $C_1$-$C_2$-alkoxycarbonyl or benzyloxycarbonyl; a group

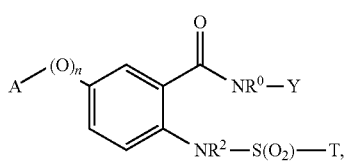

amino; or N-mono- or N,N-di-$C_1$-$C_4$-alkylamino;

$R^3$ is $C_1$-$C_4$-alkyl, unsubstituted or halogen-, $C_1$-$C_4$-alkyl- or $C_1$-$C_4$-haloalkyl-substituted phenyl, unsubstituted or halogen-, $C_1$-$C_4$-alkyl- or $C_1$-$C_4$-haloalkyl-substituted pyridyl, $C_1$-$C_4$-alkoxycarbonylmethyl or morpholin-4-yl-carbonylmethyl;

$R^0$ is H or hydroxy; and

Y is (i) phenyl or a phenylamino, which is substituted by one or more same or different radicals selected from the group consisting of halogen; $C_1$-$C_6$-alkyl; $C_1$-$C_6$-haloalkyl; $C_3$-$C_6$-cycloalkyl; $C_3$-$C_6$-halocycloalkyl; hydroxyl; $C_1$-$C_6$-alkoxy; $C_1$-$C_6$-haloalkoxy; $C_1$-$C_6$-alkylthio; $C_1$-$C_6$-haloalkylthio; $C_1$-$C_6$-alkyl-sulfinyl; $C_1$-$C_6$-haloalkylsulfinyl; $C_1$-$C_6$-alkylsulfonyl; $C_1$-$C_6$-haloalkylsulfonyl; $SF_5$; amino; N-mono- or N,N-di-$C_1$-$C_6$-alkylamino; tri-$C_1$-$C_4$-alkylsilyl; $C_1$-$C_6$-alkoxycarbonyl; aminocarbonyl; N-mono- or N,N-di-$C_1$-$C_6$-alkylaminocarbonyl; aminosulfonyl; N-mono- or N,N-di-$C_1$-$C_6$-alkylaminosulfonyl; N—$C_1$-$C_6$-alkylsulfonylamino; $C_1$-$C_6$-alkoxycarbonylamino; N—$C_1$-$C_4$-alkyl-N—$C_1$-$C_6$-alkoxycarbonylamino; cyano; nitro; and unsubstituted or halogen-, $C_1$-$C_4$-alkyl-, $C_1$-$C_4$-haloalkyl-, $C_1$-$C_4$-alkoxy-, $C_1$-$C_4$-haloalkoxy-, amino-, cyano- or nitro-substituted $C_3$-$C_6$-heterocyclyl; or is (ii) 5- or 6 membered heteroaryl or heteroarylamino, which is each further unsubstituted or substituted by halogen, cyano, nitro, $C_1$-$C_4$-alkyl, $C_1$-$C_4$-haloalkyl, $C_1$-$C_4$-alkoxy, $C_1$-$C_4$-alkoxycarbonyl, $C_2$-$C_4$-alkanoyl, or phenyl or phenylsulfonyl which is each unsubstituted or substituted by halogen, cyano, nitro methyl or methoxy; or is (iii) benzoyl or 5- or 6 membered heteroarylcarbonyl, which is each further unsubstituted or substituted by halogen, cyano, nitro, $C_1$-$C_4$-alkyl, $C_1$-$C_4$-haloalkyl, $C_1$-$C_4$-alkoxy, $C_1$-$C_4$-alkoxycarbonyl, $C_2$-$C_4$-alkanoyl or phenyl; or is (iv) a $C_6$-$C_{12}$-bicarbocyclic radical; or is a (v) a hetero-bicyclic ring radical comprising a total of 8 to 10 ring members, from which 1 to 5, preferably 1 or 2, members are same or different heteroatoms selected from the group consisting of B, N, O and S, and from which 0 to 2 members are a group —C(O)—, which bicyclic ring radical is further unsubstituted or substituted by halogen, cyano, hydroxyl, $C_1$-$C_4$-alkoxy, $C_1$-$C_4$-alkyl or $C_1$-$C_4$-haloalkyl; or is (vi) a radical $H_2C$—C(O)—NH—$R^4$, wherein $R^4$ is $C_1$-$C_4$-haloalkyl, $C_2$-$C_3$-alkynyl or cyano-$C_1$-$C_4$-alkyl; or $R^0$ and Y together with the N-atom to which they are attached, form a piperidinyl or piperazinyl radical which is substituted by $C_1$-$C_4$-alkyl, $C_1$-$C_4$-alkoxy, unsubstituted or halogen-, $C_1$-$C_4$-alkyl-, $C_1$-$C_4$-haloalkyl-, amino- and/or $C_1$-$C_4$-alkoxy-substituted phenyl or benzoylamino, or unsubstituted or $C_1$-$C_4$-alkyl-, $C_1$-$C_4$-haloalkyl-, $C_3$-$C_6$-cycloalkyl- or halogen-substituted pyridyl or pyrimidinyl;

subject to the provisos that (i) at least one of A and Y must not be a phenyl radical if T is $CH_3$; and (ii) T is $C_1$-$C_6$-alkyl which is unsubstituted or substituted as mentioned above if A is $C_1$-$C_6$-alkyl or $C_1$-$C_6$-haloalkyl.

The invention also provides a composition comprising a compound of formula (I), or a salt or enantiomer thereof, and at least one carrier, for example a surfactant, a solid diluent and/or a liquid diluent.

In one embodiment, this invention also provides a composition for controlling parasites, in particular endoparasites, comprising a biologically effective amount of a compound of formula (I), or a salt thereof, and at least one additional component selected from the group consisting of a surfactant, a solid diluent and a liquid diluent, said composition optionally further comprising a biologically effective amount of at least one additional pharmaceutically or veterinary active compound or agent.

This invention also provides a method for controlling parasites comprising contacting the parasites or their environment with a pharmaceutically or veterinary effective amount of a compound of formula (I), an enantiomer or a salt thereof, (e.g., as a composition described herein). This invention also relates to such method wherein the parasites or their environment are contacted with a composition comprising a pharmaceutically or veterinary effective amount of a compound of formula (I), an enantiomer or a salt thereof, and at least one additional component selected from the group consisting of a surfactant, a solid diluent and a liquid diluent, said composition optionally further comprising a pharmaceutically or veterinary effective amount of at least one additional pharmaceutically or veterinary active compound or agent.

This invention also provides a method for protecting an animal from a parasitic pest comprising administering to the animal a parasiticidally effective amount of a compound of formula (I), an enantiomer or a salt thereof.

DETAILS OF THE INVENTION

In the above recitations, the term "alkyl", used either alone or in compound words such as "alkylthio", "haloalkylthio", "haloalkyl", "N-alkylamino", "N,N-di-alkyamino" and the like includes straight-chain or branched alkyl, such as, methyl, ethyl, n-propyl, i-propyl, n-, iso-, sec.- or tert.-butyl or the different pentyl or hexyl isomers.

The term "alkoxy" used either alone or in compound words such as "haloalkoxy", "alkoxycarbonyl" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio, butylthio, pentylthio and hexylthio isomers.

"Alkylsulfinyl" includes both enantiomers of an alkylsulfinyl group. Examples of "alkylsulfinyl" include $CH_3S(O)$—, $CH_3CH_2S(O)$—, $CH_3CH_2CH_2S(O)$—, $(CH_3)_2CHS(O)$— and the different butylsulfinyl, pentylsulfinyl and hexylsulfinyl isomers.

"Alkylcarbonyl" denotes a straight-chain or branched alkyl moieties bonded to a C(=O) moiety. Examples of "alkylcarbonyl" include $CH_3C(=O)$—, $CH_3CH_2CH_2C(=O)$— and $(CH_3)_2CHC(=O)$—. Examples of "alkoxycarbonyl" include $CH_3OC(=O)$—, $CH_3CH_2OC(=O)$, $CH_3CH_2CH_2OC(=O)$—, $(CH_3)_2CHOC(=O)$— and the different butoxy- or pentoxycarbonyl isomers, for example tert.-butoxycarbonyl (Boc). Examples of "alkoxycarbonylamino" include tert.-butoxycarbonylamino, examples of "N-alkoxycarbonyl" include N-tert.-butoxycarbonyl and examples of "N-alkylamino" include N-methylamino. Examples of "N-mono- or N,N-di-alkylaminocarbonyl" include N-methylaminocarbonyl, N-ethylaminocarbonyl, N-methyl-N-ethylaminocarbonyl, N,N-di-methylaminocarbonyl or N,N-di-ethylaminocarbonyl. Examples of "alkylcarbonylamino" include methylcarbonylamino or ethylcarbonylamino.

Examples of "alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl, pentylsulfonyl and hexylsulfonyl isomers. Examples of "N-mono- or N,N-di-alkylaminosulfonyl" include N-methylaminosulfonyl, N-ethylaminosulfonyl, N-methyl-N-ethylaminosulfonyl, N,N-di-methylaminosulfonyl or N,N-di-ethylaminosulfonyl. Examples of "alkylsulfonylamino" include methylsulfonylamino or ethylsulfonylamino.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methycyclohexyl.

Examples of $C_6$-$C_{12}$-bicarbocyclyl are the radical of (+)- or (−)-campher (1,7,7-trimethylbicyclo[2.2.1]heptan-2-one), a radical

, a radical

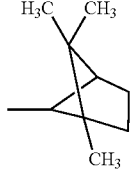

or indanyl.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$—, $ClCH_2$—, $CF_3CH_2$— and $CF_3CCl_2$—. The terms "halocycloalkyl", "haloalkoxy", "haloalkylthio", and the like, are defined analogously to the term "haloalkyl". Examples of "haloalkoxy" include $CF_3O$—, $CF_3CF_2$—O—, $CF_3CH_2O$—, $CCl_3CH_2O$—, $CF_3CHFCF_2O$— and $HCF_2CH_2CH_2O$—. Examples of "haloalkylthio" include $CCl_3S$—, $CF_3S$—, $CCl_3CH_2S$— and $ClCH_2CH_2CH_2S$—. Examples of "haloalkylsulfinyl" include $CF_3S(O)$—, $CCl_3S(O)$—, $CF_3CH_2S(O)$— and $CF_3CF_2S(O)$—. Examples of "haloalkylsulfonyl" include $CF_3S(O)_2$—, $CCl_3S(O)_2$—, $CF_3CH_2S(O)_2$— and $CF_3CF_2S(O)_2$—.

The total number of carbon atoms in a substituent group is indicated by the "$C_i$-$C_j$" prefix where i and j are integers. For example, $C_1$-$C_4$ alkylsulfonyl designates methylsulfonyl through butylsulfonyl.

When a compound is substituted with a substituent bearing a subscript that indicates the number of said substituents can exceed 1, said substituents (when they exceed 1) are independently selected from the group of defined substituents, e.g., $(R_2)_n$, n is 1 or 2.

"Aromatic" indicates that each of the ring atoms is essentially in the same plane and has ap-orbital perpendicular to the ring plane, and in which (4n+2) π electrons, where n is a positive integer, are associated with the ring to comply with Hückel's rule.

The terms "heterocyclyl", "heterocyclic ring" or "heterocycle" denote a ring in which at least one atom forming the ring backbone is not carbon, e.g., nitrogen, oxygen sulfur or a group S(O) or $S(O_2)$. Typically a heterocyclic ring contains no more than 4 nitrogens, no more than 2 oxygens and no more than 2 sulfurs. In addition, the heterocyclic ring may contain a group C(O)—, —S(O)— or —$S(O_2)$—. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "heteroaryl" substituent. Unless otherwise indicated, heterocyclic rings and ring systems can be attached through any available carbon or nitrogen by replacement of a hydrogen on said carbon or nitrogen.

The term heterocyclyl, either alone or in compound words such as heterocyclyloxy may be, for example a 5- or 6-membered heterocyclic radical having from 1 to 4, preferably from 1 to 3 same or different heteroatoms selected from the group consisting of B, N, O and S, which is further unsubstituted or substituted. Examples of suitable substituents of the heterocyclyl are halogen, $C_1$-$C_6$-alkyl, $C_1$-$C_6$-haloalkyl, $C_3$-$C_6$-cycloalkyl, $C_3$-$C_6$-halocycloalkyl, hydroxy, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, cyano, nitro, amino, N-mono- or N,N-di-$C_1$-$C_4$-alkylamino, $C_1$-$C_6$-alkoxycarbonyl, sulfonamido, N-mono- or N,N,di-$C_1$-$C_4$-alkylsulfonamido, $C_1$-$C_6$-alkylcarbonylamino, N-mono- or N,N-di-$C_1$-$C_6$-alkylaminocarbonyl, $C_2$-$C_6$-alkanoyl, or phenyl, which is unsubstituted or substituted by halogen, $C_1$-$C_6$-alkyl, $C_1$-$C_6$-haloalkyl, $C_1$-$C_6$-alkoxy, $C_1$-$C_6$-haloalkoxy, cyano or nitro.

The term heterocyclyl may denote, for example, a 5- or 6-membered heteroaryl radical having from 1 to 4, preferably from 1 to 3 same or different heteroatoms selected from the group consisting of N, O and S, which is further unsubstituted or substituted by one or more substituents as defined above for heterocyclyl. The heteroaryl radical is preferably substituted by 0 to 3, in particular 0, 1 or 2 substituents from the group as defined above.

The term 5- or 6-membered heteroaryl, either alone or in terms such as heteroarylamino or heteroarylcarbonyl, may include, for example, a thienyl, pyrryl, pyrazolyl, furyl, oxazolyl, thiazolyl, isothiazolyl, thiadiazolyl, pyridyl, pyrimidinyl or thiazinyl radical which is each unsubstituted or substituted, for example, by halogen, cyano, nitro, $C_1$-$C_2$-alkyl, $C_1$-$C_2$-haloalkyl, $C_3$-$C_6$-cycloalkyl, $C_1$-$C_4$-alkoxy, $C_2$-$C_4$-alkanoyl, $C_1$-$C_4$-alkoxycarbonyl or unsubstituted or substituted phenyl.

The term heterocyclyl may further denote a 3 to 6-membered heterocycloalkyl radical having from 1 to 3 same or different heteroatoms selected from the group consisting of B, N, O and S, which is further unsubstituted or substituted by one or more substituents as defined above for heterocyclyl. The heterocycloalkylene radical is preferably substituted by 0 to 3, in particular 0, 1 or 2 substituents from the group as defined above. Examples are tetrahydrofuranyl, pyrrolidinyl, morpholinyl, piperidinyl, piperazinyl or dioxoborolanyl which is each unsubstituted or substituted by halogen, $C_1$-$C_2$-alkyl, $C_1$-$C_2$-haloalkyl or $C_1$-$C_2$-alkoxy.

Examples of heterocyclyloxy are 2-, 3- or 4-pyridyloxy or pyrimidin-4-yloxy, which is each unsubstituted or substituted by halogen, $C_1$-$C_2$-alkyl, $C_3$-$C_6$-cycloalkyl, $C_1$-$C_2$-haloalkyl or $C_1$-$C_2$-alkoxy.

Examples of heterobicyclic ring radicals are benzoxazolyl, benzothiazolyl, tetrahydro-benzothiazolyl, indolyl, benzimidazolyl, benzopyrazolyl, 5,6-dihydro-4H-cyclopenta[b]thiophen-2-yl, methylenedioxoyphenyl, benzooxaboronyl, chinolinyl, triazolopyrimidinonyl, for example 1,2,3-triazolo[4,5-d]pyrimidin-7-one-5-yl, or phthalhydrazidyl, which may each be unsubstituted or substituted, for example, by halogen, cyano, $C_1$-$C_4$-alkyl, $C_1$-$C_2$-haloalkyl, hydroxy or $C_1$-$C_2$-alkoxy.

Concerning the variables contained in the compounds of formula (I), the following meanings and preferences apply.

The variable n is preferably 1 if A is a phenyl radical. The variable n is preferably 0 if A is different from a phenyl radical, e.g. if A is $C_1$-$C_6$-alkyl, $C_1$-$C_6$-haloalkyl, $C_3$-$C_6$-cycloalkyl; $C_3$-$C_6$-halocycloalkyl; a 5- or 6-membered heterocycloalkyl radical, a heteroaromatic radical, or a heterobicyclic ring radical.

Preferred substituents of the phenyl radical A are halogen; $C_1$-$C_4$-alkyl; $C_1$-$C_4$-haloalkyl; amino; $C_1$-$C_4$-alkoxy; $C_1$-$C_4$-haloalkoxy; $C_1$-$C_4$-haloalkylthio; $C_1$-$C_4$-alkylsulfonyl; $C_1$-$C_4$-haloalkylsulfonyl; tri-$C_1$-$C_2$-alkylsilyl; $C_1$-$C_4$-alkoxycarbonyl; N-mono- or N,N-di-$C_1$-$C_4$-alkylaminocarbonyl; aminosulfonyl; N-mono- or N,N-di-$C_1$-$C_4$-alkylaminosulfonyl; N—$C_1$-$C_2$-alkyl-N—$C_1$-$C_4$-alkoxycarbonylamino; cyano; nitro; or 5- or 6-membered heterocycloalkyl comprising 1 or 2 same or different heteroatoms selected from O, S and N, which is unsubstituted or substituted by halogen, $C_1$-$C_2$-alkyl, $C_1$-$C_2$-haloalkyl or $C_1$-$C_2$-alkoxy.

More preferred substituents of the phenyl radical A are halogen; $C_1$-$C_2$-alkyl; $C_1$-$C_4$-haloalkyl; amino; $C_1$-$C_4$-alkoxy; $C_1$-$C_4$-haloalkoxy; $C_1$-$C_4$-alkylsulfonyl; $C_1$-$C_4$-haloalkylsulfonyl; trimethylsilyl; $C_1$-$C_4$-alkoxycarbonyl; N,N-di-$C_1$-$C_2$-alkylaminocarbonyl; aminosulfonyl; N,N-di-$C_1$-$C_2$-alkylaminosulfonyl; N—$C_1$-$C_2$-alkyl-N—$C_1$-$C_4$-alkoxycarbonylamino; cyano; nitro; or a heterocycloalkyl radical selected from the group consisting of tetrahydrofuranyl, pyrrolidinyl, morpholinyl and piperidinyl.

Especially preferred substituents of the phenyl radical A are halogen, $C_1$-$C_2$-alkyl, $C_1$-$C_2$-haloalkyl, $C_1$-$C_2$-alkoxy, $C_1$-$C_2$-haloalkoxy or cyano, and especially chlorine, fluorine or $CF_3$.

Specific preferred phenyl radicals A are 2-, 3- or 4-Cl-phenyl, 4-$CF_3$-phenyl, 3,5-di-Cl-phenyl, 3,5-di-$CF_3$-phenyl, 2,4,6-tri-Cl-phenyl, 3,4,5-tri-Cl-phenyl, 2-Cl-4-$CF_3$-phenyl, 2-$CF_3$-4-Cl-phenyl or 2,6-di-Cl-4-$CF_3$-phenyl, in particular 4-Cl-phenyl.

A as $C_1$-$C_6$-alkyl is preferably $C_1$-$C_4$-alkyl. A as haloalkyl is preferably $C_1$-$C_2$-haloalkyl, in particular $CF_3$.

A as 5- or 6-membered heterocycloalkyl is preferably a pyrrolidinyl, piperazinyl, morpholinyl or dioxaborolanyl, which is each unsubstituted or substituted by methyl.

A as a heteroaromatic radical is preferably pyrryl, pyrazolyl, triazolyl, thienyl, thiazinyl, thiazolyl, pyridyl or pyrimidinyl, which is each unsubstituted or substituted by halogen, cyano, $C_1$-$C_2$-alkyl, $C_1$-$C_2$-alkoxy, $C_1$-$C_2$-haloalkyl, acetyl, propionyl, phenyl or morpholin-4-yl-methyl. Particularly preferred meanings of A as heteroaromatic radical are 2-, 3- or 4-pyridyl which is unsubstituted or substituted by halogen, cyano, $C_1$-$C_2$-alkoxy, acetyl or propionyl; pyrimidinyl which is unsubstituted or substituted by halogen or acetyl; 1,2,4-triazol-5-yl which is unsubstituted or substituted by phenyl; thienyl which is unsubstituted or substituted by halogen, acetyl or morpholin-4-yl-methyl; pyrazol-1-yl or -5-yl which is each unsubstituted or substituted by methyl; or thiazin-4-yl.

A as a hetero-bicyclic ring radical is preferably indolyl, benzopyrazolyl or benzothiazol, which is each unsubstituted or substituted by methyl.

According to a preferred embodiment of the invention A is $C_1$-$C_4$-alkyl; $C_1$-$C_2$-haloalkyl; heterocycloalkyl selected from pyrrolidinyl, piperazinyl, morpholinyl and dioxaborolanyl, which is each unsubstituted or substituted by methyl; a heteroaromatic radical selected from pyrryl, pyrazolyl, triazolyl, thienyl, thiazinyl, thiazolyl, pyridyl and pyrimidinyl, which is each unsubstituted or substituted by halogen, cyano, $C_1$-$C_2$-alkyl, $C_1$-$C_2$-alkoxy, $C_1$-$C_2$-haloalkyl, acetyl, propionyl, phenyl or morpholin-4-yl-methyl; or a hetero-bicyclic ring radical selected from indolyl, benzopyrazolyl and benzothiazol, which is each unsubstituted or substituted by methyl.

The variable $R^2$ is preferably H.

T as alkyl radical is preferably $C_1$-$C_4$-alkyl, which is unsubstituted or substituted by halogen, cyclopropyl, cyclohexyl, trimethylsilyl, carboxy or $C_1$-$C_2$-alkoxycarbonyl. Particularly preferred meanings of T as alkyl radical are $C_1$-$C_4$-alkyl; $C_1$-$C_3$-haloalkyl, in particular $CF_3$, —$CH_2$—$CF_3$ or —$CH_2$—$CH_2$—$CF_3$; trimethylsilyl-$C_1$-$C_2$-alkyl; $C_1$-$C_2$-alkoxycarbonylmethyl; carboxymethyl; or cyclohexylmethyl; especially methyl.

T as $C_3$-$C_6$-cycloalkyl, in preferably cyclopropyl or cyclohexyl.

T as bicarbocyclyl is, for example, a bicycloalkylene or bicycloalkylenone radical, for example 1,7,7-trimethylbicyclo[2.2.1]heptyl or 1,7,7-trimethylbicyclo[2.2.1]heptan-2-one-yl ((+)- or (−)-camphor).

T as phenyl radical is preferably phenyl which is unsubstituted or substituted by fluorine, chlorine, methyl, methoxy, $CF_3$ or nitro.

T as heteroaromatic radical is preferably pyridyl, thienyl or pyrimidinyl.

T as heterocycloalkyl is preferably piperidinyl, piperazinyl, tetrahydropyranyl, morpholinyl, thiomorpholinyl or thiomorpholin-4-yl-1,1-dioxide, which is each unsubstituted or substituted by methyl or benzyloxycarbonyl. Particularly preferred heterocyclyl radicals T are 1-methylpiperazin-4-yl, 1-(benzyloxycarbonyl)-piperazin-4-yl, tetrahydro-2H-pyran-4-yl or, thiomorpholin-4-yl-1,1-dioxide.

$R^3$ is preferably methyl, halophenyl, trifluoromethylpyridyl, tert.-butoxycarbonylmethyl or morpholin-4-yloxycarbonylmethyl.

T is preferably $C_1$-$C_4$-alkyl; $C_1$-$C_3$-haloalkyl; trimethylsilyl-$C_1$-$C_2$-alkyl; $C_1$-$C_2$-alkoxycarbonylmethyl; carboxymethyl; cyclohexylmethyl; $C_3$-$C_6$-cycloalkyl; 1,7,7-trimethylbicyclo[2.2.1]heptyl or 1,7,7-trimethylbicyclo[2.2.1]heptan-2-one-yl((+)- or (−)-camphor); phenyl which is unsubstituted or substituted by fluorine, chlorine, methyl, methoxy, $CF_3$ or nitro; pyridyl, thienyl or pyrimidinyl; heterocycloalkyl selected from piperidinyl, piperazinyl, tetrahydropyranyl, morpholinyl, thiomorpholinyl or thiomorpholin-4-yl-1,1-dioxide, which is each unsubstituted or substituted by methyl or benzyloxycarbonyl; or a group

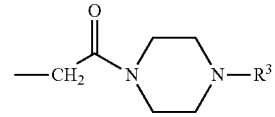

wherein $R^3$ is methyl, halophenyl, trifluoromethylpyridyl, tert.-butoxycarbonylmethyl or morpholin-4-yloxycarbonylmethyl.

$R^0$ is preferably H.

Preferred substituents of the phenyl or phenylamino radical Y are halogen; $C_1$-$C_4$-alkyl; $C_1$-$C_4$-haloalkyl; $C_3$-$C_6$-cycloalkyl; $C_1$-$C_4$-alkoxy; $C_1$-$C_4$-haloalkoxy; $C_1$-$C_4$-haloalkylthio; $SF_5$; N,N-di-$C_1$-$C_4$-alkylamino-$C_1$-$C_4$-alkylaminocarbonyl; N—$C_1$-$C_4$-alkylsulfonylamino; cyano; nitro; hydroxy; $B(OH)_2$ or methylsulfonylamino.

More preferred substituents of the phenyl or phenylamino radical Y are halogen; $C_1$-$C_2$-alkyl; $C_1$-$C_3$-haloalkyl; $C_1$-$C_2$-alkoxy; $C_1$-$C_3$-haloalkoxy; $C_1$-$C_2$-haloalkylthio; $SF_5$; cyano; nitro; hydroxy; or methylsulfonylamino.

Particularly preferred substituents of the phenyl or phenylamino radical Y halogen, methyl, $C_1$-$C_3$-haloalkyl, methoxy, $C_1$-$C_3$-haloalkoxy, $SCF_3$, $SF_5$, cyano, nitro or hydroxy and especially halogen or $CF_3$.

A specific preferred phenyl radical Y is 3,4,5-trichlorophenyl, 3,5-di-trifluoromethyl-4-chlorophenyl and 3,5-di-trifluoromethylphenyl.

A specific preferred phenylamino radical Y is phenyl amino which is substituted by chlorine, bromine, methyl trifluoromethyl, methoxy, cyano or nitro.

A heteroaryl radical Y is, for example, pyrryl, pyrazolyl, oxazolyl, thienyl, thiazolyl, isothiazolyl, thiadiazolyl, pyridyl or pyrimidinyl, which is each unsubstituted or substituted by halogen, cyano, nitro, $C_1$-$C_4$-alkyl, $C_1$-$C_2$-haloalkyl, $C_1$-$C_2$-alkoxy, $C_1$-$C_2$-alkoxycarbonyl, or phenyl or phenylsulfonyl which is in turn each unsubstituted or substituted by halogen, cyano, nitro methyl or methoxy.

A heteroaryl radical Y is preferably 2-, 3- or 4-pyridyl which is unsubstituted or substituted by halogen, $C_1$-$C_4$-alkyl or $C_1$-$C_2$-alkoxy; 2-thienyl, which is unsubstituted or substituted by $C_1$-$C_2$-alkyl or $C_1$-$C_2$-alkoxycarbonyl; 2-thiazolyl, which is unsubstituted or substituted by halogen, cyano, nitro, $C_1$-$C_2$-alkyl, $C_1$-$C_2$-haloalkyl, $C_1$-$C_2$-alkoxycarbonyl, or phenyl or phenylsulfonyl which is in turn each unsubstituted opr substituted by halogen, cyano, nitro or methyl; 5-isothiazoyl which is unsubstituted or substituted by halogen or methyl; 2-oxazolyl, which is unsubstituted or substituted by $C_1$-$C_2$-alkyl or $C_1$-$C_2$-haloalkyl; or 1,3,4-thiadiazol-5-yl, which is unsubstituted or substituted by $C_1$-$C_2$-alkyl or $C_1$-$C_2$-haloalkyl.

A heteroarylamino radical Y is preferably 2-, 3- or 4-pyridylamino, which is unsubstituted or substituted by halogen, $C_1$-$C_4$-alkyl or $C_1$-$C_2$-alkoxy.

A benzoyl or heteroarylcarbonyl radical Y is preferably benzoyl, which is unsubstituted or substituted by halogen; or 2-, 3- or 4-pyridylcarbonyl which is unsubstituted or substituted by halogen or $C_1$-$C_4$-alkyl.

A preferred bicarbocyclic radical Y is preferably a radical

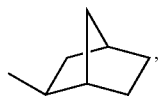

a radical

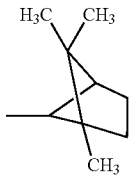

or indanyl.

A preferred heterobicyclic ring radical Y is benzothiazolyl, indolyl, chinolinyl, methylenedioxophenyl, benzooxaboronyl, triazolopyrimidinonyl or phthalhydrazidyl, which is each be unsubstituted or substituted by halogen, $C_1$-$C_4$-alkyl, $C_1$-$C_2$-haloalkyl, $C_1$-$C_4$-alkoxy or hydroxy.

The variable $R^4$ is preferably propynyl, 2,2,2-trifluoroethyl or cyanomethyl.

A preferred radical Y is thus (i) phenyl or phenylamino which is substituted by halogen, $C_1$-$C_2$-alkyl, $C_1$-$C_3$-haloalkyl, $C_1$-$C_2$-alkoxy, $C_1$-$C_3$-haloalkoxy, $C_1$-$C_2$-haloalkylthio, $SF_5$, cyano, nitro, hydroxy or methylsulfonylamino; (iia) heteroaryl selected from 2-, 3- or 4-pyridyl which is unsubstituted or substituted by halogen, $C_1$-$C_4$-alkyl or $C_1$-$C_2$-alkoxy, 2-thienyl, which is unsubstituted or substituted by $C_1$-$C_2$-alkyl or $C_1$-$C_2$-alkoxycarbonyl, 2-thiazolyl, which is unsubstituted or substituted by halogen, cyano, nitro, $C_1$-$C_2$-alkyl, $C_1$-$C_2$-haloalkyl, $C_1$-$C_2$-alkoxycarbonyl, or phenyl or phenylsulfonyl which is in turn each unsubstituted or substituted by halogen, cyano, nitro or methyl, 5-isothiazoyl which is unsubstituted or substituted by halogen or methyl, 2-oxazolyl, which is unsubstituted or substituted by $C_1$-$C_2$-alkyl or $C_1$-$C_2$-haloalkyl, or 1,3,4-thiadiazol-5-yl, which is unsubstituted or substituted by $C_1$-$C_2$-alkyl or $C_1$-$C_2$-haloalkyl; (iib) heteroarylamino selected from 2-, 3- or 4-pyridylamino, which is unsubstituted or substituted by halogen, $C_1$-$C_4$-alkyl or $C_1$-$C_2$-alkoxy; (iii) benzoyl, which is unsubstituted or substituted by halogen, or 2-, 3- or 4-pyridylcarbonyl which is unsubstituted or substituted by halogen or $C_1$-$C_4$-alkyl; (iv) a bicarbocyclic radical selected from a radical

a radical

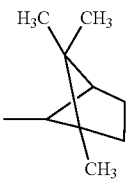

and indanyl; (v) a heterobicyclic ring radical selected from benzothiazolyl, indolyl, chinolinyl, methylenedioxophenyl, benzooxaboronyl, triazolopyrimidinonyl and phthalhydrazidyl, which is each be unsubstituted or substituted by halogen, $C_1$-$C_4$-alkyl, $C_1$-$C_2$-haloalkyl, $C_1$-$C_4$-alkoxy or hydroxy; or (vi) a radical $H_2C$—$C(O)$—$NH$—$R^4$, wherein $R^4$ is propynyl, 2,2,2-trifluoroethyl or cyanomethyl.

If $R^0$ and Y together with the N-atom to which they are attached, form a piperidinyl or piperazinyl radical, said piperidinyl or piperazinyl radical is preferably substituted by methyl; methoxy; halogen-, amino-, methoxy- or trifluoromethyl-substituted phenyl or benzoylamino; or halogen-, trifluoromethyl- and/or cyclopropyl-substituted pyridyl or pyrimidinyl.

One embodiment of the present invention concerns a compound of formula

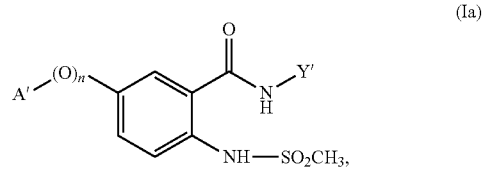

(Ia)

wherein n has the above-given meaning including the preferences, Y' is phenyl which is substituted as mentioned above including the preferences; and A' is $C_1$-$C_6$-alkyl; $C_1$-$C_6$-haloalkyl; $C_3$-$C_6$-cycloalkyl; $C_3$-$C_6$-halocycloalkyl; 5- or 6-membered heterocycloalkyl having from 1 to 3 same or different heteroatoms selected from the group consisting of B, N, O and S, which is further unsubstituted or substituted by halogen, $C_1$-$C_4$-alkyl or $C_1$-$C_4$-alkoxy; a heteroaromatic radical, which is further unsubstituted or substituted by halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkanoyl, 5- or 6-membered heterocycloalkyl-$C_1$-$C_2$-alkyl or unsubstituted or halogen-, $C_1$-$C_4$-alkyl- or $C_1$-$C_4$-alkoxy-substituted phenyl; or is a hetero-bicyclic ring radical comprising a total of 8 to 10 ring members, from which 1 to 5, preferably 1 or 2, members are same or different heteroatoms selected from the group consisting of B, N, O and S, and from which 0 to 2 members are a group C(O)—, which bicyclic ring radical is further unsubstituted or substituted by halogen, cyano, hydroxyl, $C_1$-$C_4$-alkoxy, $C_1$-$C_4$-alkyl or $C_1$-$C_4$-haloalkyl.

A compound of formula (Ia), wherein Y' is phenyl which is substituted by 2 or 3 same or different radicals selected from halogen or $CF_3$; and A' is $C_1$-$C_4$-alkyl; $CF_3$; pyrrolidinyl, piperazinyl, morpholinyl or dioxaboronalanyl, which is each unsubstituted or substituted by methyl; pyrryl, pyrazolyl, triazolyl, thienyl, thiazinyl, thiazolyl, pyridyl or pyrimidinyl, which is each unsubstituted or substituted by halogen, cyano, $C_1$-$C_2$-alkyl, $C_1$-$C_2$-alkoxy, $C_1$-$C_2$-haloalkyl, acetyl, propionyl, phenyl or morpholin-4-yl-methyl; or indolyl, benzopyrazolyl or benzothiazolyl, which is each unsubstituted or substituted by methyl or methoxy; and n is 0 or 1, in particular 1; is especially preferred.

A further preferred embodiment of the present invention concerns a compound of formula

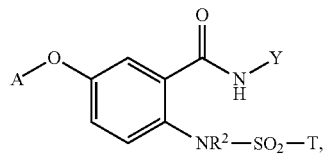

(Ib)

wherein A is phenyl which is unsubstituted or substituted as mentioned above including the preferences, Y is phenyl which is substituted as mentioned above including the preferences, T is $C_2$-$C_6$-alkyl, which is unsubstituted or substituted by halogen, trimethylsilyl, $C_3$-$C_6$-cycloalkyl, carboxy or $C_1$-$C_4$-alkoxycarbonyl; $C_3$-$C_6$-cycloalkyl; $C_6$-$C_{12}$-bicarbocyclyl; phenyl which is unsubstituted or substituted by halogen, cyano, nitro, $C_1$-$C_4$-alkyl, $C_1$-$C_4$-haloalkyl or $C_1$-$C_4$-alkoxy; a 5- or 6 membered heteroaromatic radical, which is further unsubstituted or substituted by halogen, $C_1$-$C_4$-alkyl or $C_1$-$C_4$-alkoxy; amino; N-mono- or N,N-di-$C_1$-$C_4$-alkylamino; 5- or 6-membered heterocycloalkyl having from 1 to 3 same or different heteroatoms selected from the group consisting of N, O, S and S($O_2$), which is further unsubstituted or substituted by $C_1$-$C_4$-alkyl; or a group

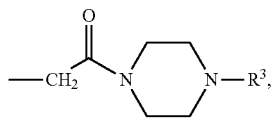

and $R^3$ is $C_1$-$C_4$-alkyl, unsubstituted or halogen-, $C_1$-$C_4$-alkyl- or $C_1$-$C_4$-haloalkyl-substituted phenyl, unsubstituted or halogen-, $C_1$-$C_4$-alkyl- or $C_1$-$C_4$-haloalkyl-substituted pyridyl, $C_1$-$C_4$-alkoxycarbonylmethyl or morpholin-4-yl-carbonylmethyl.

A preferred embodiment relates to a compound of formula (Ib), wherein A is phenyl which is unsubstituted or preferably mono-substituted by chlorine, fluorine or $CF_3$, Y is phenyl which is substituted by 2 or 3 same or different radicals selected from halogen or $CF_3$, and T is $C_2$-$C_4$-alkyl, which is unsubstituted or substituted by halogen, cyclopropyl, cyclohexyl, trimethylsilyl, carboxy or $C_1$-$C_2$-alkoxycarbony; cyclopropyl or cyclohexyl; the radical of (+)- or (−)-camphor; phenyl which is unsubstituted or substituted by fluorine, chlorine, methyl, methoxy, $CF_3$ or nitro; or pyridyl, thienyl or pyrimidinyl; piperidinyl, piperazinyl, tetrahydropyranyl, morpholinyl, thiomorpholinyl or thiomorpholin-4-yl-1,1-dioxide, which is each unsubstituted or substituted by methyl or benzyloxycarbonyl.

A further preferred embodiment of the present invention concerns a compound of formula

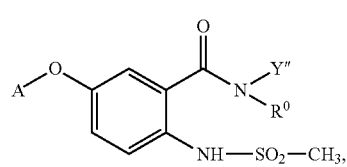

(Ic)

wherein A is phenyl which is unsubstituted or substituted as mentioned above including the preferences, $R^0$ is H or hydroxyl; and Y" is (i) 5- or 6 membered heteroaryl or heteroarylamino, which is each further unsubstituted or substituted by halogen, cyano, nitro, $C_1$-$C_4$-alkyl, $C_1$-$C_4$-haloalkyl, $C_1$-$C_4$-alkoxy, $C_1$-$C_4$-alkoxycarbonyl, $C_1$-$C_4$-alkanoyl or phenyl or phenylsulfonyl which is each unsubstituted or substituted by halogen, cyano, nitro methyl or methoxy; or is (ii) benzoyl or 5- or 6 membered heteroarylcarbonyl, which is each further unsubstituted or substituted by halogen, cyano, nitro, $C_1$-$C_4$-alkyl, $C_1$-$C_4$-haloalkyl, $C_1$-$C_4$-alkoxy, $C_1$-$C_4$-alkoxycarbonyl, $C_1$-$C_4$-alkanoyl or phenyl; or is (iii) a $C_6$-$C_{12}$-bicarbocyclic radical; or is a (iv) a hetero-bicyclic ring radical comprising a total of 8 to 10 ring members, from which 1 to 5, preferably 1 or 2, are same or different heteroatoms selected from the group consisting of B, N, O and S, and from which 0 to 2 are a group C(O)—, which bicyclic ring radical is further unsubstituted or substituted by halogen, cyano, hydroxyl, $C_1$-$C_4$-alkyl, $C_1$-$C_4$-alkoxy or $C_1$-$C_4$-haloalkyl; or is (v) a radical $H_2C$—C(O)—NH—$R^4$, wherein $R^4$ is $C_1$-$C_4$-haloalkyl, $C_2$-$C_3$-alkynyl or cyano-$C_1$-$C_4$-alkyl; or $R^0$ and Y together with the N-atom to which they are attached, form a piperidinyl or piperazinyl radical which is substituted by $C_1$-$C_4$-alkyl, $C_1$-$C_4$-alkoxy, unsubstituted or halogen-, $C_1$-$C_4$-alkyl-, halo-$C_1$-$C_4$-alkyl-, amino- and/or $C_1$-$C_4$-alkoxy-substituted phenyl or benzoylamino, or unsubstituted or $C_1$-$C_4$-alkyl-, $C_1$-$C_4$-haloalkyl-, $C_3$-$C_6$-cycloalkyl- or halogen-substituted pyridyl or pyrimidinyl.

Concerning a preferred embodiment of the compounds of formula (Ic), A is phenyl which is unsubstituted or preferably mono-substituted by chlorine, fluorine or $CF_3$; $R^0$ is H, and Y" is (i) 2-, 3- or 4-pyridyl which is unsubstituted or substituted by halogen, $C_1$-$C_4$-alkyl or $C_1$-$C_2$-alkoxy; 2-thienyl, which is unsubstituted or substituted by $C_1$-$C_2$-alkyl, $C_1$-$C_2$-alkoxycarbonyl; 2-thiazolyl, which is unsubstituted or substituted by halogen, cyano, nitro, $C_1$-$C_2$-alkyl, $C_1$-$C_2$-haloalkyl, $C_1$-$C_2$-alkoxycarbonyl, or phenyl or phenylsulfonyl which is in turn each unsubstituted opr substituted by halogen, cyano, nitro or methyl; 5-isothiazoyl which is unsubstituted or substituted by halogen or methyl; 2-oxazolyl, which is unsubstituted or substituted by $C_1$-$C_2$-alkyl or $C_1$-$C_2$-haloalkyl; or 1,3,4-thiadiazol-5-yl, which is unsubstituted or substituted by $C_1$-$C_2$-alkyl or $C_1$-$C_2$-haloalkyl; 2-, 3- or 4-pyridylamino, which is unsubstituted or substituted by halogen, $C_1$-$C_4$-alkyl or $C_1$-$C_4$-alkoxy; or (ii) benzoyl, which is unsubstituted or substituted by halogen or 2-, 3- or 4-pyridylcarbonyl which is unsubstituted or substituted by halogen or $C_1$-$C_4$-alkyl; or (iii) a radical

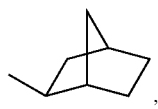, a radical

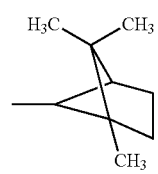

or indanyl; or (iv) benzothiazolyl, indolyl, chinolinyl, methylenedioxo-phenyl, benzooxaboronyl, triazolopyrimidinonyl or phthal-hydrazidyl, which is each be unsubstituted or substituted by halogen, $C_1$-$C_4$-alkyl, $C_1$-$C_2$-haloalkyl or hydroxy; or (v) a radical $H_2C-C(O)-NH-CH_2-C\equiv CH$, $H_2C-C(O)-NH-CH_2-CN$ or $H_2C-C(O)-NH-CH_2-CF_3$; or $R^0$ and Y together with the N-atom to which they are attached, form a piperidinyl or piperazinyl radical, which is substituted by methyl; methoxy; halogen-, amino-, methoxy- or trifluoromethyl-substituted phenyl or benzoyl-amino; or halogen-, trifluoromethyl- and/or cyclopropyl-substituted pyridyl or pyrimidinyl.

A salt of a compound or formula (I) may be produced in known manner. Acid addition salts, for example, are obtainable by treatment with a suitable acid or a suitable ion exchange reagent, and salts with bases are obtainable by treatment with a suitable base or a suitable ion exchange reagent.

Salts of compounds of formula (I) can be converted into the free compounds by the usual means, acid addition salts e.g. by treating with a suitable basic composition or with a suitable ion exchange reagent, and salts with bases e.g. by treating with a suitable acid or a suitable ion exchange reagent.

Salts of compounds of formula (I) can be converted into other salts of compounds of the formula (I) in a known manner; acid addition salts can be converted for example into other acid addition salts, e.g. by treating a salt of an inorganic acid, such as a hydrochloride, with a suitable metal salt, such as a sodium, barium, or silver salt, of an acid, e.g. with silver acetate, in a suitable solvent, in which a resulting inorganic salt, e.g. silver chloride, is insoluble and thus precipitates out from the reaction mixture.

Depending on the method and/or reaction conditions, the compounds of formula (I) with salt-forming characteristics can be obtained in free form or in the form of salts. Compounds of formula (I) can also be obtained in the form of their hydrates and/or also can include other solvents, used for example where necessary for the crystallisation of compounds present in solid form.

As mentioned before, the compounds of formula (I) may be optionally present as optical and/or geometric isomers or as a mixture thereof. The invention relates both to the pure isomers and to all possible isomeric mixtures, and is hereinbefore and hereinafter understood as doing so, even if stereochemical details are not specifically mentioned in every case.

Diastereoisomeric mixtures of compounds of formula (I), which are obtainable by the process or in another way, may be separated in known manner, on the basis of the physical-chemical differences in their components, into the pure diastereoisomers, for example by fractional crystallisation, distillation and/or chromatography.

Splitting of mixtures of enantiomers, that are obtainable accordingly, into the pure isomers, may be achieved by known methods, for example by recrystallisation from an optically active solvent, by chromatography on chiral adsorbents, e.g. high-pressure liquid chromatography (HPLC) on acetyl cellulose, with the assistance of appropriate microorganisms, by cleavage with specific immobilised enzymes, through the formation of inclusion compounds, e.g. using chiral crown ethers, whereby only one enantiomer is complexed.

The compounds of the formula (I), wherein n is 0, may be prepared, for example, by reaction of a compound of formula

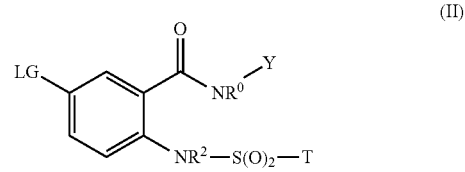

wherein $R^0$, $R^2$, T and Y are each as defined above and LG is a leaving group, for example halogen such as bromine, with a compound of formula

in the presence of a palladium catalyst, wherein A is defined above. The details of this palladium-catalyzed carbon-carbon bond forming reaction, called Suzuki reaction, are known from textbooks of organic chemistry.

The compounds of formula (II) are known or may be prepared according to known processes, for example by reacting a compound of formula

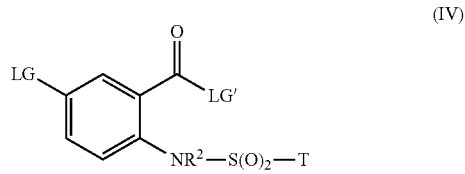

with a compound of formula

wherein LG' is a leaving group, for example halogen, $C_1$-$C_2$-alkoxy or hydroxyl, and the further variables each have the above mentioned meaning. The amide formation from an carboxylic acid or an derivative thereof with an amine is known from textbooks of organic chemistry. The compounds of formula (IV) are known or may be prepared according to known processes, for example by reacting the corresponding amine with methane sulfonyl chloride in known manner. The compounds of formula (III) and (V) are known compounds which are commercially available.

Certain compounds of the formula (I), wherein n is 0, may also be prepared, for example, by reaction of a compound of formula

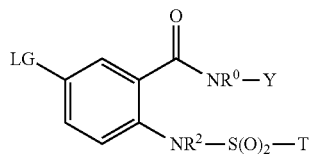

(IIa)

wherein $R^0$, $R^2$, T and Y are each as defined above and LG is a leaving group, for example halogen such as bromine or chlorine, with a compound of formula

(IIIa)

wherein A* is a heterocyclic radical A and the H-atom is attached to a heteroatom, for example N or O, by way of an electrophilic substitution at the phenyl ring. The compounds of formula (IIa) may be obtained in analogy to the compounds of formula of formula (II) above.

The compounds of the formula (I), wherein n is 1, may be prepared, for example, by reaction of a compound of formula (VI)

with a compound of formula (VII)

wherein the variables are as defined above, followed by the reduction of the nitro group and further reacting the resulting amine with methane sulfonyl chloride. The details of these reactions are known from textbooks of organic chemistry. The compounds of formula (VI) may be prepared in analogy to the compounds of formula (II). The compounds of formula (VII) are known per se and are commercially available.

The compounds of the formula (I), wherein n is 1 may also be prepared by reaction of a compound of formula

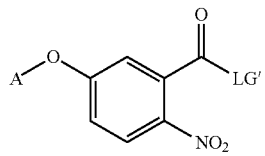

(VIII)

with a compound of formula (V)

wherein the variables each have the above given meaning, followed by the reduction of the nitro group and further reacting the resulting amine with methane sulfonyl chloride. In the alternative, the nitro group of the compound of formula (VIII) may first of all be reduced and the resulting amino group be reacted with methane sulfonyl chloride, before the reaction with the compound of formula (V) is performed.

The compounds of formula (VIII) may be prepared in a manner known per se, for example by reaction of a compound of formula (IX)

with a compound of formula (VIIa)

The Examples further illustrate the different synthesis methods.

The compounds of formula (I) according to the invention are notable for their broad activity spectrum and are valuable active ingredients for use in pest control, including in particular the control of endoparasites, especially helminths, in and on warm-blooded animals, especially productive livestock and pets, whilst being well-tolerated by warm-blooded animals and fish.

Productive livestock includes mammals such as, for example, cattle, horses, sheep, pigs, goats, donkeys, rabbits, deer, as well as birds, for example chickens, geese, turkeys, ducks and exotic birds.

Pets include, for example, dogs, cats and hamsters, in particular dogs and cats. The compounds of formula (I) of the present invention are effective against helminths, in which the endoparasitic nematodes and trematodes may be the cause of serious diseases of mammals and poultry. Typical nematodes of this indication are: Filariidae, Setariidae, *Haemonchus, Trichostrongylus, Ostertagia, Nematodirus, Cooperia, Ascaris, Bunostonum, Oesophagostonum, Charbertia, Trichuris, Strongylus, Trichonema,*

*Dictyocaulus, Capillaria, Heterakis, Toxocara, Ascaridia, Oxyuris, Ancylostoma, Uncinaria, Toxascaris* and *Parascaris*. The trematodes include, in particular, the family of Fasciolideae, especially *Fasciola hepatica* (liver fluke).

It could also be shown surprisingly and unexpectedly that the compositions of the present invention have exceptionally high efficacy against nematodes that are resistant to many active substances. This can be demonstrated, for example in vitro by the LDA test.

Certain pests of the species *Nematodirus, Cooperia* and *Oesophagostonum* infest the intestinal tract of the host animal, while others of the species *Haemonchus* and *Ostertagia* are parasitic in the stomach and those of the species *Dictyocaulus* are parasitic in the lung tissue. Parasites of the families and may be found in the internal cell tissue and in the organs, e.g. the heart, the blood vessels, the lymph vessels and the subcutaneous tissue. A particularly notable parasite is the heartworm of the dog, *Dirofilaria immitis*. The compounds of formula (I) according to the present invention are highly effective against these parasites.

The pests which may be controlled by the compounds of formula (I) of the present invention also include those from the class of Cestoda (tapeworms), e.g. the families Mesocestoidae, especially of the genus *Mesocestoides*, in particular *M. lineatus*; Dipylidiidae, especially *Dipylidium caninum, Joyeuxiella* spp., in particular *Joyeuxiella pasquali*, and *Diplopylidium* spp., and Taeniidae, especially *Taenia pisiformis, Taenia cervi, Taenia ovis, Taeneia hydatigena, Taenia multiceps, Taenia taeniaeformis, Taenia serialis*, and *Echinococcus* spp., most preferably *Taenia hydatigena, Taenia ovis, Taenia multiceps, Taenia serialis; Echinococcus granulosus* and *Echinococcus multilocularis*.

Furthermore, the compounds of formula (I) are suitable for the control of human pathogenic parasites. Of these, typical representatives that appear in the digestive tract are those of the genus *Ancylostoma, Necator, Ascaris, Strongyloides, Trichinella, Capillaria, Trichuris* and *Enterobius*. The compounds of the present invention are also effective against parasites of the genus *Wuchereria, Brugia, Onchocerca* and *Loa* from the family of *Dracunculus* and parasites of the genus *Strongyloides* and *Trichinella*, which infect the gastrointestinal tract in particular.

The good endoparasiticidal activity of the compounds of formula (I) corresponds to a mortality rate of at least 50-60%, in particular at least 80% and especially at least 90% of the endoparasites mentioned.

Administration of the compounds of formula (I) according to the invention may be effected therapeutically or preferably prophylactically.

Application of the compounds of formula (I) according to the invention to the animals to be treated may take place, for example, topically, perorally, parenterally or subcutaneously. A preferred embodiment of the invention relates to compounds of formula (I) for parenteral use or, in particular, for peroral use.

Preferred application forms for usage on warm-blooded animals in the control of nematodes/helminths comprise solutions; emulsions including classical emulsions, microemulsions and self-emulsifying compositions, that are waterless organic, preferably oily, compositions which form emulsions—together with body fluids—upon addition to an animal body; suspensions (drenches); pour-on formulations; food additives; powders; tablets including effervescent tablets; boli; capsules including micro-capsules; and chewable treats; whereby the physiological compatibility of the formulation excipients must be taken into consideration. Particularly preferred application forms are tablets, capsules, food additives or chewable treats.

The compounds of formula (I) of the present invention are employed in unmodified form or preferably together with adjuvants conventionally used in the art of formulation and may therefore be processed in a known manner to give, for example, emulsifiable concentrates, directly dilutable solutions, dilute emulsions, soluble powders, powder mixtures, granules or microencapsulations in polymeric substances. As with the compositions, the methods of application are selected in accordance with the intended objectives and the prevailing circumstances.

The formulation, i.e. the agents, preparations or compositions containing the one or more active ingredients and optionally a solid or liquid adjuvant, are produced in a manner known per se, for example by intimately mixing and/or grinding the active ingredients with the adjuvants, for example with solvents, solid carriers and/or surface-active compounds (surfactants).

The solvents in question may be: alcohols, such as ethanol, propanol or butanol, and glycols and their ethers and esters, such as propylene glycol, dipropylene glycol ether, ethylene glycol, ethylene glycol monomethyl or -ethyl ether, ketones, such as cyclohexanone, isophorone or diacetanol alcohol, strong polar solvents, such as N-methyl-2-pyrrolidone, dimethyl sulfoxide or dimethylformamide, or water, vegetable oils, such as rape, castor, coconut, or soybean oil, and also, if appropriate, silicone oils.

Suitable surfactants are, for example, non-ionic surfactants, such as, for example, nonylphenolpolyethoxyethanols; castor oil polyglycol ethers, for example macrogol glycerolhydroxystearate 40; polyethylene glycols; polypropylene/polyethylene oxide adducts; or fatty acid esters of polyoxyethylene sorbitan, e.g. polyoxyethylene sorbitan monooleate.

Solid carriers, for example for tablets and boli, may be chemically modified polymeric natural substances that are soluble in water or in alcohol, such as starch, cellulose or protein derivatives (e.g. methyl cellulose, carboxymethyl cellulose, ethylhydroxyethyl cellulose, proteins such as zein, gelatin and the like), as well as synthetic polymers, such as polyvinyl alcohol, polyvinyl pyrrolidone etc. The tablets also contain fillers (e.g. starch, microcrystalline cellulose, sugar, lactose etc.), glidants and disintegrants.

If the anthelminthics are present in the form of feed concentrates, then the carriers used are e.g. performance feeds, feed grain or protein concentrates. Such feed concentrates or compositions may contain, apart from the active ingredients, also additives, vitamins, antibiotics, chemotherapeutics or other pesticides, primarily bacteriostats, fungistats, coccidiostats, or even hormone preparations, substances having anabolic action or substances which promote growth, which affect the quality of meat of animals for slaughter or which are beneficial to the organism in another way.

Suitable compositions of the compounds of formula (I) may also contain further additives, such as stabilisers, antioxidants, for example tocopherols like α-tocopherol, antifoaming agents, viscosity regulators, binding agents, colors or tackifiers, as well as other active ingredients, in order to achieve special effects. Preferably, the composition comprises from 0.001 to 1% w/v of one or more antioxidants. If desired, the formulations of the present invention may comprise a color, for example in an amount of from 0.001 to 1% w/v.

As a rule, an anthelminthic composition according to the invention contains 0.1 to 99% by weight, especially 0.1 to 95% by weight of a compound of formula (I), 99.9 to 1% by weight, especially 99.8 to 5% by weight of a solid or liquid admixture, including 0 to 25% by weight, especially 0.1 to 25% by weight of a surfactant.

In each of the processes according to the invention for pest control or in each of the pest control compositions according to the invention, the compounds of formula (I) can be used in all of their steric configurations or in mixtures thereof.

The invention also includes a method of prophylactically protecting warm-blooded animals, especially productive livestock and pets, in particular dogs or cats, against parasitic helminths, which is characterised in that a compound of formula (I) or the active ingredient formulation prepared therefrom is administered to the warm-blooded animal as an additive to the feed, or to the drinks or also in solid or liquid form, orally or by injection or parenterally. The invention also includes the compounds of formula (I) according to the invention for usage in one of the said processes.

The compounds of formula (I) according to the invention may be used alone or in combination with other biocides. They may be combined with pesticides having the same sphere of activity e.g. to increase activity, or with substances having another sphere of activity e.g. to broaden the range of activity. It can also be sensible to add so-called repellents.

The following Examples illustrate the invention further.

Analysis of the purified samples is in each case done using a Waters Autopurification (HPLC/MS) system with a reversed phase column using method B described below. The samples are characterized by m/z and retention time. The above-given retention times relate in each case to the use of a solvent system comprising two different solvents, solvent A: $H_2O+0.01\%$ HCOOH, and solvent B: $CH_3CN+0.01\%$ HCOOH).

Method B: column Waters XTerra MS C18 μm, 50×4.6 mm (Waters), flow rate of 3.00 mL/min with a time-dependent gradient as given in the Table:

| Time [min] | A [%] | B [%] |
|---|---|---|
| 0 | 90 | 10 |
| 0.5 | 90 | 10 |
| 2.5 | 5 | 95 |
| 2.8 | 5 | 95 |
| 2.9 | 90 | 10 |
| 3.0 | 90 | 10 |

Example 1A

Synthesis of 2-(methylsulfonamido)-5-morpholino-N-(3,4,5-trichlorophenyl)benzamide (Ex. 1.2 in Table 1)

Step A: 5-chloro-2-nitro-N-(3,4,5-trichlorophenyl)benzamide 5-chloro-2-nitrobenzoic acid (10 g) was treated with thionyl chloride (7.2 mL) at reflux for 4 h. Excess $SOCl_2$ was removed under vacuum. $CH_2Cl_2$ (100 mL) was added to the acyl chloride. At 0° C., 3,4,5-trichloroaniline (9.7 g) and $NEt_3$ (13.8 mL) in 100 mL $CH_2Cl_2$ were added slowly. The reaction mixture was allowed to warm up and it was stirred at rt (room temperature) overnight. The reaction mixture was diluted with 200 mL diethyl ether. 10 mL HCl 2 N and 200 mL $H_2O$ were added, and the mixture was stirred until a yellow precipitate is formed. The precipitate was filtered off and dried under high vacuum before analysis (yield: 66%). LCMS (method B): 380.59 $(M+H)^+$ at 1.97 min.

Step B: 5-morpholino-2-nitro-N-(3,4,5-trichlorophenyl)benzamide

To a solution of 300 mg of 5-chloro-2-nitro-N-(3,4,5-trichlorophenyl)benzamide in 1.5 nil, DMF, was added morpholine (206 μL). The reaction mixture was heated at 110° C. for 1.5 h. After work-up and extraction with AcOEt, the mixture was evaporated to dryness. The title compound was pure enough to be engaged in step B. (yield: 71%). LCMS (method B): 427.7 $(M-H)^-$ at 1.81 min.

Step C: 2-amino-5-morpholino-N-(3,4,5-trichlorophenyl)benzamide

Under $N_2$, 5-morpholino-2-nitro-N-(3,4,5-trichlorophenyl)benzamide (230 mg) in 4 mL $EtOH/H_2O$ (3/1) was treated with Fe (208 mg) and HCl 25% (4 μL) and the reaction mixture was stirred at rt for 4 h. When the reduction was completed, the reaction mixture was filtered on a plug of celite and washed with ethyl acetate. The filtrate was evaporated under vacuum. Ethyl acetate was added, and the organic layer was washed with brine, dried over $MgSO_4$, and evaporated to dryness (yield: 95%). LCMS (method B): 399.68 $(M+H)^+$ at 1.61 min.

Step D: 2-(methylsulfonamido)-5-morpholino-N-(3,4,5-trichlorophenyl)benzamide

A $N_2$ degassed solution of 2-amino-5-morpholino-N-(3,4,5-trichlorophenyl)benzamide (193 mg) in 3 mL $CH_2Cl_2$, pyridine (0.194 mL) was added. The mixture was cooled to 0° C. before the drop wise addition of methane sulfonyl chloride (0.037 mL). The reaction mixture was stirred overnight at rt, then diluted with 50 mL ethyl acetate. The organic layer was washed with a saturated solution of $Na_2CO_3$, with brine, then dried over $MgSO_4$ and evaporated to dryness (yield: 43%). LCMS (method B): 477.7 $(M+H)^+$ at 1.78 min.

Example 1B

N-(3,5-bis (trifluoromethyl) phenyl)-5-(2-fluoropyridin-3-yl)-2-(methylsulfonamido) benzamide (Ex. 1.14 in Table 1)

Step A: methyl 5-bromo-2-(methylsulfonamido) benzoate

A $N_2$ degassed solution of methyl 2-amino-5-bromobenzoate (2.8 g) in 10 mL 1 pyridine was cooled to 0° C. before the drop wise addition of methane sulfonyl chloride (0.9 mL). The reaction mixture was stirred overnight at rt, then diluted with 50 mL ethyl acetate. The organic layer was washed with a saturated solution of $Na_2CO_3$, with brine, then dried over $MgSO_4$ and evaporated to dryness (yield: 82%). LCMS (method B): 305.6 $(M-H)^-$ at 1.55 min.

Step B: 5-bromo-2-(methylsulfonamido)benzoic acid

Methyl 5-bromo-2-(methylsulfonamido) benzoate (3.15 g) was suspended in THF (20 mL, 1/1). NaOH 4 N (6.9 mL) was added and the reaction mixture was stirred 4 h at reflux. Upon completion, the reaction mixture was treated with 2N HCl (1 mL) and extracted twice with ethyl acetate. Combined organic layers were washed with H₂O, brine, dried over Na₂SO₄, filtered and evaporated to dryness. The title product was pure enough by LCMS to be engaged into next step without further purification. (yield: 66%) LCMS (method B): 291.64 (M−H)⁻ at 1.2 min.

Step C: N-(3,5-bis(trifluoromethyl)phenyl)-5-bromo-2-(methylsulfonamido)benzamide 5-bromo-2-(methylsulfonamido) benzoic acid (2.4 g) was treated with thionyl chloride (23 mL) at reflux for 4 h. Excess SOCl₂ was removed under vacuum. CH₂Cl₂ (20 mL) was added to the acyl chloride. At 0° C., 3,5-bis(trifluoromethyl)aniline (1.4 mL) and NEt₃ (5.68 mL) in 10 mL CH₂Cl₂ were added slowly. The reaction mixture was allowed to warm up and it was stirred at rt overnight.

The reaction mixture was diluted with 30 mL CH₂Cl₂. 20 mL HCl 2 N and 20 mL H₂O were added, and the mixture was stirred until a yellow precipitate is formed. The precipitate was filtered off and dried under high vacuum before analysis (yield: 67%). LCMS (method B): 502.93 (M−H)⁻ at 1.99 min.

Step D: N-(3,5-bis (trifluoromethyl) phenyl)-5-(2-fluoropyridin-3-yl)-2-(methylsulfonamido) benzamide To a solution of N-(3,5-bis(trifluoromethyl)phenyl)-5-bromo-2-(methylsulfonamido) benzamide (0.2 g) and 2-Fluoro-3-(4,4,5,5-tetramethyl-1,3,2-dioxaborolan-2-yl) pyridine (133 mg) under N₂ in dioxane/H₂O (6 mL, 1/1) was added Na₂CO₃ (252 mg), Pd(dppf)Cl₂·CH₂Cl₂ (355 mg). The reaction mixture was stirred for 3 h at 80° C. It was diluted with ethyl acetate, filtered through celite. The filtrate was washed with H₂O, brine, dried over Na₂SO₄, filtered and evaporated to dryness.

The crude mixture was purified by flash chromatography eluting with a gradient of 100% heptane to 60% heptane/40% ethyl acetate to offer the title compound in 25% yield. LCMS (method C): 521.8 (M+H)⁺ at 1.90 min.

The substances named in the following Table 1 are prepared analogously to the above-described methods. The compounds are of formula

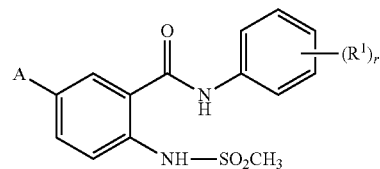

wherein the meaning of A and (R¹)ᵣ is given in Table 1.

The following physical data are obtained according to the above-described HPLC/MS characterization process (method B). Rₜ refers to "retention time".

TABLE 1

| Ex. No. | A | (R¹)ᵣ | m/z: [M + H⁺] | Rₜ [min] (Method B) | Physical state |
|---|---|---|---|---|---|
| 1.2 | Morpholin-4-yl | 3,4,5-tri-Cl | 477.7 | 1.78 | Solid |
| 1.3 | 4-Methylpiperazin-1-yl | 3,4,5-tri-Cl | 490.9 | 1.29 | Solid |
| 1.4 | Thiazin-4-yl | 3,4,5-tri-Cl | 493.7 | 1.97 | Solid |
| 1.5 | Pyrrolidin-1-yl | 3,4,5-tri-Cl | 461.7 | 2.04 | Foam |
| 1.6 | Pyrazol-1-yl | 3,4,5-tri-Cl | 458.8 | 1.89 | Powder |
| 1.7 | Isopropyl | 3,5-di-CF₃ | 468.8 | 2.07 | Powder |
| 1.8 | CF₃ | 3,5-di-CF₃ | 494.5 | 1.99 | Oil |
| 1.9 | pinacol boronate ester group | 3,5-di-CF₃ | 552.9 | 2.22 | Powder |
| 1.10 | 5-methyl-2-acetylthiophene group | 3,5-di-CF₃ | 550.7 | 1.99 | Powder |
| 1.11 | 1,3,4,5-tetramethylpyrazol-4-yl | 3,5-di-CF₃ | 534.8 | 1.78 | Solid |
| 1.12 | 1,5-dimethylpyrazol-4-yl | 3,5-di-CF₃ | 506.7 | 1.79 | Powder |

TABLE 1-continued
| Ex. No. | A | $(R^1)_r$ | m/z: [M + H⁺] | $R_t$ [min] (Method B) | Physical state |
|---|---|---|---|---|---|
| 1.13 | 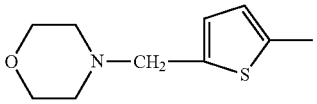 | 3,5-di-CF₃ | 607.9 | 1.27 | Resin |
| 1.14 | 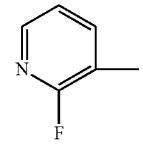 | 3,5-di-CF₃ | 521.8 | 1.90 | Powder |
| 1.15 | 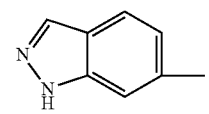 | 3,5-di-CF₃ | 542.8 | 1.85 | Powder |
| 1.16 | 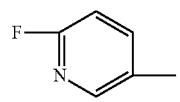 | 3,5-di-CF₃ | 521.7 | 1.94 | Powder |
| 1.17 | 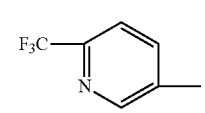 | 3,5-di-CF₃ | 571.7 | 2.06 | Foam |
| 1.18 | 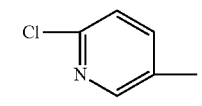 | 3,5-di-CF₃ | 537.7 | 2.00 | Powder |
| 1.19 | 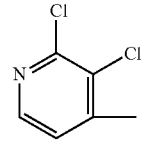 | 3,5-di-CF₃ | 571.6 | 2.10 | Powder |
| 1.20 | 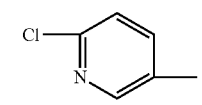 | 3,5-di-CF₃ | 551.7 | 2.06 | Powder |
| 1.21 | 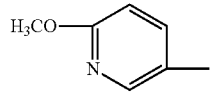 | 3,5-di-CF₃ | 533.7 | 2.02 | Powder |
| 1.22 | 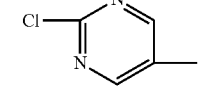 | 3,5-di-CF₃ | 538.7 | 1.93 | Powder |
| 1.23 | 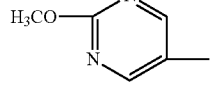 | 3,5-di-CF₃ | 534.7 | 1.85 | Powder |
| 1.24 | 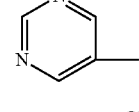 | 3,5-di-CF₃ | 504.8 | 1.71 | Powder |
| 1.25 | 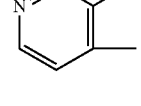 | 3,5-di-CF₃ | 537.8 | 1.90 | Solid |

TABLE 1-continued

| Ex. No. | A | $(R^1)_r$ | m/z: [M + H⁺] | $R_t$ [min] (Method B) | Physical state |
|---|---|---|---|---|---|
| 1.26 | 2,4-dimethyl-thiazole (H₃C, CH₃ on thiazole) | 3,5-di-CF₃ | 537.8 | 1.89 | Foam |
| 1.27 | 2-ethoxy-pyridin-5-yl (H₃C—H₂C—O-pyridine) | 3,5-di-CF₃ | 548.0 | 2.08 | Powder |
| 1.28 | 2-cyano-pyridin-5-yl (NC-pyridine) | 3,5-di-CF₃ | 529.0 | 1.89 | Powder |
| 1.29 | 2-chloro-pyridin-3-yl | 3,5-di-CF₃ | 537.9 | 1.94 | Powder |
| 1.30 | 5-chloro-thiophen-2-yl | 3,5-di-CF₃ | 542.9 | 2.28 | Powder |
| 1.31 | 4-trifluoromethyl-pyrimidin-2-yl | 3,5-di-CF₃ | 572.9 | 2.11 | Powder |
| 1.32 | 2-trifluoromethyl-pyridin-4-yl | 3,5-di-CF₃ | 571.8 | 2.05 | Powder |
| 1.33 | 2-chloro-pyridin-4-yl | 3,5-di-CF₃ | 537.7 | 1.99 | Resin |

Example 2

5-phenoxy-2-(phenylsulfonamido)-N-(3,4,5-trichlorophenyl)benzamide (Ex. 2.2 in Table 2)

Step A: 2-nitro-5-phenoxy-N-(3,4,5-trichlorophenyl) benzamide

5-Chloro-2-nitro-N-(3,4,5-trichlorophenyl) benzamide (29.1 g), K₂CO₃ (21.3 g) and phenol (8 g) in DMA were heated at 140° C. during 14 h. The reaction mixture was poured in H₂O (100 mL), the precipitate was filtered off, dried under high vacuum to afford a brown solid (yield: 80%). LCMS (method B): 436.6 (M–H)⁻ at 2.14 min.

Step B: 2-amino-5-phenoxy-N-(3,4,5-trichlorophenyl)benzamide 2-nitro-5-phenoxy-N-(3,4,5-trichlorophenyl)benzamide treated with iron in a similar manner as described for step C Example 1 (yield: 27%). LCMS (method B): 406.7 (M+H)⁺ at 2.28 min.

Step C: 5-(4-Chlorophenoxy)-2-(methylsulfona-mido)-N-(3,4,5-trichlorophenyl) benzamide To $N_2$ degassed solution of 2-amino-5-phenoxy-N-(3,4,5-trichlorophenyl)benzamide (0.26 mg) in 2 mL of $CH_2Cl_2$, pyridine (0.25 mL) was added. The mixture was cooled to 0° C. before the drop wise addition of benzene sulfonyl chloride (0.124 mg). The reaction mixture was stirred overnight at rt, then diluted with additional 5 mL $CH_2Cl_2$. The organic layer was washed with a saturated solution of $Na_2CO_3$, with brine, then dried over $MgSO_4$ and evaporated to dryness (yield: 81%). LCMS (method B): 546.7 $(M+H)^+$ at 2.39 min.

The substances named in the following Table 2 are prepared analogously to the above-described methods. The compounds are of formula

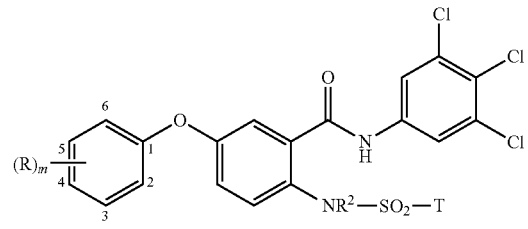

wherein the meaning of $(R^1)_r$, $(R)_m$, and X are given in Table 2

The following physical data are obtained according to the above-described HPLC/MS characterization process (Method B).

TABLE 2

| Ex. No. | $(R)_m$ | T | $R^2$ | m/z: $[M + H^+]$ | $R_t$ [min] | Physical state |
|---|---|---|---|---|---|---|
| 2.1 | 4-Cl | 4-$CH_3$-phenyl | | 594.6 | 2.22 | Powder |
| 2.2 | H | phenyl | H | 546.7 | 2.39 | Powder |
| 2.3 | 4-Cl | 2-$NO_2$-4-$CF_3$-phenyl | H | 693.6 | 1.88 | Gum |
| 2.4 | 4-Cl | 3-Cl-4-F-phenyl | H | 632.5 | 2.57 | Solid |
| 2.5 | 4-Cl | 2-$CF_3$-4-F-phenyl | H | 666.5 | 2.59 | Solid |
| 2.6 | 4-Cl | 4-$CF_3$-phenyl | H | 648.5 | 2.58 | Solid |
| 2.7 | 4-Cl | 3,4-dimethoxyphenyl | H | 640.6 | 2.40 | Solid |
| 2.8 | 4-Cl | 4-nitrophenyl | H | 625.5 | 2.46 | Solid |
| 2.9 | 4-Cl | 4-chlorophenyl | H | 614.7 | 2.59 | Solid |
| 2.10 | 4-Cl | 3,5-di-Cl-phenyl | H | 648.5 | 2.78 | Solid |
| 2.11 | 4-Cl | 4-methoxyphenyl | H | 610.6 | 2.46 | Solid |
| 2.12 | 4-Cl | 2-Chloro-phenyl | H | 614.5 | 2.57 | Solid |
| 2.13 | 4-Cl | 3-Chlorophenyl | H | 614.7 | 2.60 | Solid |
| 2.14 | 4-Cl | 3-Pyridyl | H | 581.6 | 2.31 | Solid |
| 2.15 | 4-Cl | 3-methoxyphenyl | H | 610.6 | 2.49 | Solid |
| 2.16 | 4-Cl | 3,4-dichlorophenyl | H | 648.5 | 2.71 | Solid |
| 2.17 | 4-Cl | 2,6-dichlorophenyl | H | 648.6 | 2.66 | Solid |
| 2.18 | 4-Cl | 2-methoxyphenyl | H | 610.6 | 2.43 | Solid |
| 2.19 | 4-Cl | 2,4-dichlorophenyl | H | 648.6 | 2.74 | Solid |
| 2.20 | 4-Cl | 2-$NO_2$-4-$OCH_3$-phenyl | H | 655.5 | 2.42 | Powder |
| 2.21 | 4-Cl | 2,4-dimethoxyphenyl | H | 640.6 | 2.41 | Solid |
| 2.22 | 4-Cl | ethyl | H | 532.5 | 2.37 | Solid |
| 2.23 | 4-Cl | —$CH_2CF_3$ | H | 586.4 | 2.39 | Powder |
| 2.24 | 4-Cl | —$CH_2CH_2CF_3$ | H | 598.5 | 2.47 | Solid |
| 2.25 | 4-Cl | n-propyl | H | 546.6 | 2.44 | Solid |
| 2.26 | 4-Cl | n-butyl | H | 560.7 | 2.52 | Solid |
| 2.27 | 4-Cl | Iso-butyl | H | 560.7 | 2.51 | Powder |
| 2.28 | 4-Cl | —$CH_2CH_2Si(CH_3)_3$ | H | 604.7 | 2.68 | Powder |
| 2.29 | 4-Cl | Cyclopropyl | H | 544.6 | 2.36 | Powder |
| 2.30 | 4-Cl | Cyclohexyl | H | 586.6 | 2.65 | Powder |
| 2.31 | 4-Cl | 1-(benzyloxycarbonyl)-piperazin-4-yl | H | 721.8 | 2.54 | Powder |
| 2.32 | 4-Cl | Isopropyl | H | 546.6 | 2.23 | Solid |
| 2.33 | 4-Cl | Cyclohexylmethyl | H | 600.6 | 2.74 | Solid |
| 2.34 | 4-Cl | (1R)-(−)-Campher | H | 654.7 | 2.57 | Solid |
| 2.35 | 4-Cl | —$CH_2C(O)OC_2H_5$ | H | 590.6 | 2.36 | Solid |
| 2.36 | 4-Cl | —$CH_2C(O)OCH_3$ | H | 576.6 | 2.29 | Foam |
| 2.37 | 4-Cl | —$CH_2C(O)OH$ | H | 562.5 | 2.16 | Solid |
| 2.38 | 4-Cl | (1S)-(+)-Campher | H | 654.8 | 2.55 | Solid |
| 2.39 | 4-Cl | Tetrahydro-2H-pyran-4-yl | H | 588.6 | 2.33 | Solid |
| 2.40 | 4-Cl | —$N(CH_3)_2$ | H | 547.6 | 2.40 | Powder |
| 2.41 | 4-Cl | 1-Methylpiperazin-4-yl | H | 602.8 | 1.72 | Powder |
| 2.42 | 4-Cl | (thiomorpholine-1,1-dioxide-N-methyl) | H | 637.6 | 2.24 | Powder |
| 2.43 | 4-Cl | —$CH_2$—Cl | —$SO_2CH_2Cl$ | 664.4 | 2.44 | Solid |

TABLE 2-continued

| Ex. No. | (R)_m | T | R² | m/z: [M + H⁺] | R_t [min] | Physical state |
|---|---|---|---|---|---|---|
| 2.44 | 4-Cl | —CH₂—C(O)—N(piperazine)N—CH₃ | H | 644.6 | 1.52 | Powder |
| 2.45 | 4-Cl | —CH₂—C(O)—N(piperazine)N-(pyridin-2-yl with 5-CF₃) | H | 775.6 | 2.63 | Powder |
| 2.46 | 4-Cl | —CH₂—C(O)—N(piperazine)N—CH₂—C(O)—N(morpholine) | H | 757.8 | 1.59 | Powder |
| 2.47 | 4-Cl | —CH₂—C(O)—N(piperazine)N—CH₂—C(O)—O—C(CH₃)₃ | H | 744.7 | 2.41 | Powder |
| 2.48 | 4-Cl | —CH₂—C(O)—N(piperazine)N-(4-chlorophenyl) | H | 740.6 | 2.68 | Powder |

Example 3

2-(methylsulfonamido)-N-(3,4,5-trichlorophenyl)-5-((2-(trifluoromethyl)pyridin-3-yl)oxy)benzamide (Ex 3.2 in Table 3)

Step A: methyl 2-nitro-5-((2-(trifluoromethyl) pyridin-3-yl)oxy)benzoate

Methyl 5-chloro-2-nitrobenzoate was treated in a similar manner as step A of synthesis of example 3 (yield: 28%). LCMS (method B): 342.86 (M+H)⁺ at 1.63 min.

Step B: 2-nitro-5-((2-(trifluoromethyl) pyridin-3-yl)oxy)benzoic acid

Methyl 2-nitro-5-((2-(trifluoromethyl) pyridin-3-yl)oxy)benzoate (277 mg) was treated overnight at rt with NaOH 1N (4.13 mL) in THF/MeOH (8 mL, 2/1) (yield: 98%). LCMS (method B): 328.84 (M+H)⁺ at 1.33 min.

Step C: 2-nitro-N-(3,4,5-trichlorophenyl)-5-((2-(trifluoromethyl)pyridin-3-yl)oxy) benzamide 2-nitro-5-((2-(trifluoromethyl) pyridin-3-yl) oxy) benzoic acid was treated in a similar manner as step A of synthesis of example 1 (yield: 45%). LCMS (method B): 505.7 (M+H)⁺ at 2.05 min.

Step D: 2-amino-N-(3,4,5-trichlorophenyl)-5-((2-(trifluoromethyl)pyridine-3-yl)oxy) benzamide 2-nitro-N-(3,4,5-trichlorophenyl)-5-((2-(trifluoromethyl) pyridin-3-yl) oxy) benzamide was treated in a similar manner as step C Example 1 (yield: 100%). LCMS (method B): 475.52 (M+H)⁺ at 2.21 min.

Step E: 2-(methylsulfonamido)-N-(3,4,5-trichlorophenyl)-5-((2-(trifluoromethyl)pyridin-3-yl)oxy) benzamide 2-amino-N-(3,4,5-trichlorophenyl)-5-((2-(trifluoromethyl) pyridine-3-yl) oxy) benzamide was treated in a similar manner as step D of synthesis of example 1 (yield: 20%). LCMS (method C): 553.7 (M+H)⁺ at 2.07 min.

The substances named in the following Table 3 are prepared analogously to the above-described methods. The compounds are of formula

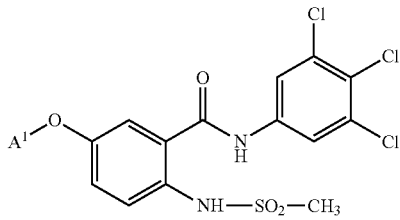

wherein the meaning of A¹ given in Table 3. The following physical data are obtained according to the above-described HPLC/MS characterization process.

TABLE 3

| Ex. No. | A¹ | m/z: [M + H⁺] | $R_t$ [min] (Method) | $R_t$ [min] (Method) |
|---|---|---|---|---|
| 3.1 | 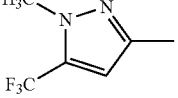 | 556.7 | 2.09 (B) | Solid |
| 3.2 | 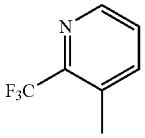 | 553.7 | 2.07 (B) | Solid |
| 3.3 | 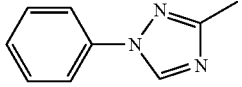 | 551.7 | 3.95 (A) | Foam |
| 3.4 | 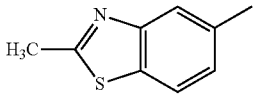 | 558.8 | 2.95 (C) | Solid |

Example 4

5-(4-chlorophenoxy)-2-(methylsulfonamido)-N-(4-(trifluoromethyl)oxazol-2-yl)benzamide (Ex 4.16 in Table 4)

Step A: methyl 5-(4-chlorophenoxy)-2-nitrobenzoate methyl 5-chloro-2-nitrobenzoate was treated in a similar manner as step A of synthesis of example 3 (yield: 90%). LCMS (method B): 305.0 (M+H)⁺ at 1.67 min.

Step B: methyl 2-amino-5-(4-chlorophenoxy)benzoate methyl 5-(4-chlorophenoxy)-2-nitrobenzoate was treated in a similar manner as step C Example 1 (yield: 100%). LCMS (method B): 277.82 (M+H)⁺ at 1.88 min.

Step C: methyl 5-(4-chlorophenoxy)-2-(methylsulfonamido)benzoate methyl 2-amino-5-(4-chlorophenoxy)benzoate was treated in a similar manner as step D of synthesis of example 1 (yield: 95%). LCMS (method B): 353.78 (M–H)⁻ at 1.84 min.

Step D: 5-(4-chlorophenoxy)-2-(methylsulfonamido)benzoic acid methyl 5-(4-chlorophenoxy)-2-(methylsulfonamido)benzoate was saponified in a similar manner as step B of synthesis of example 4 (yield: 96%). LCMS (method B): 339.62 (M–H)⁻ at 1.61 min.

Step E: 5-(4-chlorophenoxy)-2-(methylsulfonamido)-N-(4-(trifluoromethyl) oxazol-2-yl)benzamide 5-(4-chlorophenoxy)-2-(methylsulfonamido) benzoic acid was treated in a similar manner as step A of synthesis of example 1 (yield: 3%). LCMS (method B): 475.64 (M+H)⁺ at 1.70 min.

The substances named in the following Table 4 are prepared analogously to the above-described methods. The compounds are of formula

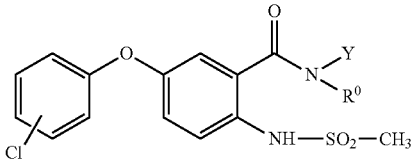

wherein the meaning of Y and R⁰ is given in Table 4. The following physical data are obtained according to the above-described HPLC/MS characterization process (Method B).

TABLE 4

| Ex. No. | Y | R⁰ | m/z: [M + H⁺] | $R_t$ [min] (Method) | $R_t$ [min] (Method B) |
|---|---|---|---|---|---|
| 4.1 | 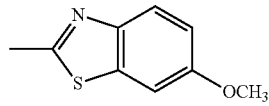 | H | 503.7 | 1.94 | Powder |
| 4.2 | 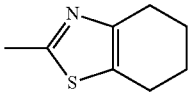 | H | 447.7 | 1.99 | Solid |
| 4.3 | 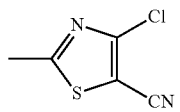 | H | 482.6 | 1.94 | Solid |
| 4.4 | 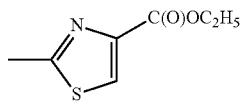 | H | 495.6 | 1.76 | Solid |

TABLE 4-continued

| Ex. No. | Y | R⁰ | m/z: [M + H⁺] | $R_t$ [min] (Method) | $R_t$ [min] (Method B) |
|---|---|---|---|---|---|
| 4.5 | 2-methylthiazole | H | 423.6 | 1.69 | Solid |
| 4.6 | 2-methyl-5-nitrothiazole | H | 468.6 | 1.79 | Powder |
| 4.7 | 2-methyl-5-(trifluoromethyl)-1,3,4-thiadiazole | H | 492.7 | 1.83 | Solid |
| 4.8 | 3-cyano-2-methyl-5,6-dihydro-4H-cyclopenta[b]thiophene | H | 487.6 | 1.99 | Solid |
| 4.9 | ethyl 2,4-dimethylthiazole-5-carboxylate | H | 509.7 | 1.95 | Solid |
| 4.10 | 2-methyl-5-((4-nitrophenyl)sulfonyl)thiazole | H | 608.6 | 1.85 | Solid |
| 4.11 | ethyl 4,5-dimethylthiophene-3-carboxylate | H | 508.6 | 2.32 | Solid |
| 4.12 | ethyl 2-methyl-4-(trifluoromethyl)thiazole-5-carboxylate | H | 563.6. | 2.00 | Solid |
| 4.13 | 5-methyl-3-(trichloromethyl)-1,2,4-thiadiazole | H | 540.5 | 2.05 | Solid |
| 4.14 | ethyl 2-methyl-4-phenylthiazole-5-carboxylate | H | 571.7 | 2.20 | Solid |
| 4.15 | 3,5-dimethylisothiazole | H | 437.7 | 1.67 | Solid |
| 4.16 | 2-methyl-4-(trifluoromethyl)oxazole | H | 475.6 | 1.70 | Oil |

TABLE 4-continued

| Ex. No. | Y | R⁰ | m/z: [M + H⁺] | R_t [min] (Method) | R_t [min] (Method B) |
|---|---|---|---|---|---|
| 4.17 | 5-methyl-2-methoxypyridinyl | H | 417.8 | 1.45 | Oil |
| 4.18 | 5-methylpyridin-3-yl | H | 447.7 | 2.20 | Oil |
| 4.19 | 3-chloro-2,4-dimethylpyridinyl | H | 465.7 | 1.47 | Oil |
| 4.20 | 2-chloro-3-methylpyridinyl | H | 451.7 | 1.71 | Oil |
| 4.21 | 5-tert-butyl-6-methylpyridin-2-yl | H | 485.8 | 1.90 | Oil |
| 4.22 | 2,4-dimethylpyridinyl | H | 431.7 | 1.25 | Powder |
| 4.23 | 2,2-difluoro-5-methylbenzo[d][1,3]dioxol-yl | H | 496.9 | 2.06 | Foam |
| 4.24 | 6-methyl-2-(trifluoromethyl)benzo[d]thiazolyl | H | 541.7 | 2.07 | Solid |
| 4.25 | 2-tert-butyl-6-methylbenzo[d]thiazolyl | H | 543.8 | 2.09 | Solid |
| 4.26 | 1-hydroxy-5-methyl-1,3-dihydrobenzo[c][1,2]oxaborolyl | H | 472.7 | 1.62 | Solid |
| 4.27 | 4-methyl-1H-indolyl | H | 455.8 | 1.71 | Solid |

TABLE 4-continued
| Ex. No. | Y | R⁰ | m/z: [M + H⁺] | R_t [min] (Method) | R_t [min] (Method B) |
|---|---|---|---|---|---|
| 4.28 | 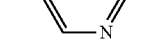 | H | 467.8 | 1.73 | Solid |
| 4.29 | 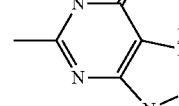 | H | 475.8 | 1.51 | Solid |
| 4.30 | 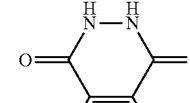 | H | 500.8 | 1.77 | Solid |
| 4.31 | 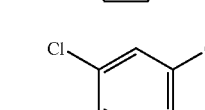 | H | 567.6 | 2.08 | Solid |
| 4.32 | 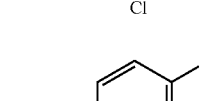 | H | 510.7 | 1.78 | Solid |
| 4.33 | 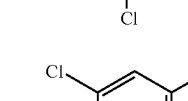 | H | 533.6 | 2.09 | Oil |
| 4.34 | 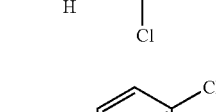 | H | 479.7 | 1.89 | Powder |
| 4.35 | 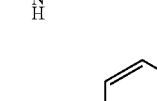 | H | 461.8 | 1.78 | Oil |
| 4.36 | 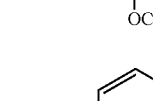 | H | 465.7 | 1.82 | Oil |

TABLE 4-continued

| Ex. No. | Y | R⁰ | m/z: [M + H⁺] | $R_t$ [min] (Method) | $R_t$ [min] (Method B) |
|---|---|---|---|---|---|
| 4.37 | 3,4-dichlorophenyl-NH-CH₂- | H | 499.7 | 1.89 | Oil |
| 4.38 | 4-cyanophenyl-NH-CH₂- | H | 456.7 | 1.65 | Oil |
| 4.39 | 4-bromophenyl-NH-CH₂- | H | 509.7 | 1.75 | Oil |
| 4.40 | dipropyl(methyl)amino- |  | 423.7 | 0.61 | Powder |
| 4.41 | dipropyl(4-methoxyphenyl)amino- |  | 515.7 | 1.67 | Foam |
| 4.42 | 4-(dipropylamino)-6-(trifluoromethyl)-2-cyclopropylpyrimidinyl |  | 595.7 | 1.93 | Powder |
| 4.43 | N-(1-methoxypropyl-pentyl)-4-amino-5-chloro-2-methoxybenzamide |  | 636.8 | 1.62 | Solid |
| 4.44 | -H₂C-C(O)-NH-CH₂-C≡CH | H | 435.7 | 1.48 | Solid |
| 4.45 | -H₂C-C(O)-NH-CH₂-CF₃ | H | 479.7 | 1.56 | Solid |
| 4.46 | -H₂C-C(O)-NH-CH₂-C≡N | H | 436.7 | 1.46 | Solid |
| 4.47 | 2,6-difluorophenyl ketone | H | 480.7 | 1.74 | Oil |

TABLE 4-continued

| Ex. No. | Y | R⁰ | m/z: [M + H⁺] | $R_t$ [min] (Method) | $R_t$ [min] (Method B) |
|---|---|---|---|---|---|
| 4.48 | 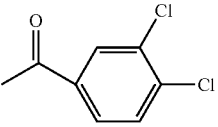 | H | 512.7 | 1.85 | Solid |
| 4.49 | 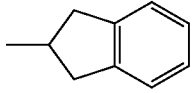 | H | 456.8 | 1.95 | Resin |
| 4.50 | 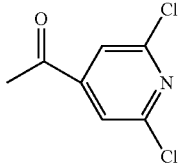 | H | 513.7 | 1.76 | Solid |
| 4.51 | 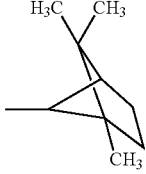 | H | 477.0 | 3.09 | Foam |
| 4.52 |  | H | 434.8 | 2.02 | Oil |
| 4.53 |  | OH | 481.7 | 3.27 | Solid |

Biological Examples

Gastro-Intestinal Larval Development Assay

Freshly harvested and cleaned nematode eggs are used to seed a suitably formatted well plate containing the test substances to be evaluated for antiparasitic activity and media allowing the full development of eggs through to 3rd instar larvae. The plates are incubated for 6 days at 25° C. and 60% relative humidity. Egg-hatching and ensuing larval development are recorded to identify a possible nematodicidal activity. Efficacy is expressed in percent reduced egg hatch, reduced development of L3, or paralysis & death of larvae at any stage. Compounds Nos. 1.4, 1.10-1.12, 1.14, 1.16-1.21, 1.23, 1.25-1.26, 1.29-1.33, 2.1, 2.22, 2.28, 2.42-2.43, 3.1-3.2, 4.1, 4.3-4.8, 4.19-4.24, 4.28, 4.32, 4.34, 4.36-4.37, 4.39, 4.42-4.43 and 4.51 reached ≥60% efficacy at 10 ppm, and are therefore considered active.

Dirofilaria immitis Microfilaria Assay

Freshly harvested and cleaned Dirofilaria immitis microfilariae are prepared from blood from donor animals dogs. The microfilariae are then distributed in formatted microplates containing the test substances to be evaluated for antiparasitic activity. The plates are incubated for 48 hours at 25° C. and 60% relative humidity (RH). Motility of microfilariae is then recorded to determine efficacy. Efficacy is expressed in percent reduced motility as compared to the control and standards. Compounds Nos. 1.2-1.4 and 1.6 to 1.33, 2.1-2.20, 2.22-2.44, 2.46, 3.1-3.4, 4.1-4.10, 4.12-4.16, 4.17-4.18, 4.21-4.29, 4.31-4.39, 4.42 and 4.46-4.52 showed an efficacy above 50% at 10 ppm, and are therefore considered active.

Acanthocheilonema viteae in Gerbil

Gerbils are artificially infected with 80 L3 larvae of A. viteae by subcutaneous injection. Treatment by gavage with the formulated test compounds occurs consecutively day 5 to day 9 after infection. Eighty-four days after infection, gerbils are bled for counting circulating microfilariae, using a Fuchs-Rosenthal counting chamber and microscope. Only test groups with an average of circulating microfilariae at least 50% lower than in the placebo treated group are fully dissected to recover adult worms. Efficacy is expressed as a % reduction in worm numbers in comparison with the placebo treated group, using the Abbot's formula. Compound No. 1.6-1.8, 1.17, 1.25, 1.30, 1.32, 2.24, 4.13, 4.24 showed an efficacy above 80% at 10 mg/kg.

Adult Liver Fluke—In Vitro Assay

Freshly harvested adult Fasciola hepatica from cattle or sheep livers were distributed in 12-well plates (1 fluke per well) with 4 mL of RPMI complete medium and kept in an incubator at 37° C. for approximately 12 hours. After renewal of the medium, the viability of the flukes is determined by video-registration of the movement of the individual flukes (pre-value). Test compounds are added at a concentration of 100 μg/mL and the movements of the flukes are measured after 6 and 24 hours. Efficacy is expressed as percent reduced movement based on the pre-value and the untreated control. In this test the following examples showed more than >90% efficacy after 6 h and >95% after 24 h are considered as positive: 2.2, 4.13.

We claim:

1. A compound of formula

(I)

or a salt or an enantiomer thereof, wherein
n is 1;
A is a phenyl radical which is substituted by chlorine, fluorine or $CF_3$;
$R^2$ is H or —$S(O_2)$-T;
T is $C_1$-$C_6$-alkyl which is unsubstituted or substituted by halogen, trimethylsilyl, $C_3$-$C_6$-cycloalkyl, carboxyl or $C_1$-$C_4$-alkoxycarbonyl; $C_3$-$C_6$-cycloalkyl; $C_6$-$C_{12}$-bicarbocyclyl; phenyl which is unsubstituted or substituted by halogen, cyano, nitro, $C_1$-$C_4$-alkyl, $C_1$-$C_4$-haloalkyl or $C_1$-$C_4$-alkoxy; a 5- or 6 membered heteroaromatic radical, which is further unsubstituted or substituted by halogen, cyano, nitro, $C_1$-$C_4$-alkyl, $C_1$-$C_4$-haloalkyl or $C_1$-$C_4$-alkoxy; 5- or 6-membered heterocycloalkyl having from 1 to 3 same or different heteroatoms selected from the group consisting of N, O, S and $S(O_2)$, which is further unsubstituted or substituted by $C_1$-$C_4$-alkyl, $C_1$-$C_2$-alkoxycarbonyl or benzyloxycarbonyl; a group

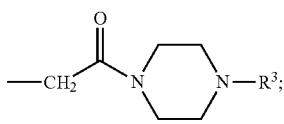

amino; or N-mono- or N,N-di-$C_1$-$C_4$-alkylamino;
$R^3$ is $C_1$-$C_4$-alkyl, unsubstituted or halogen-, $C_1$-$C_4$-alkyl- or $C_1$-$C_4$-haloalkyl-substituted phenyl, unsubstituted or halogen-, $C_1$-$C_4$-alkyl- or $C_1$-$C_4$-haloalkyl-substituted pyridyl, $C_1$-$C_4$-alkoxycarbonyl-methyl or morpholin-4-yl-carbonylmethyl;
$R^0$ is H or hydroxy; and
Y is
(i) phenyl or a phenylamino, which is substituted by one or more same or different radicals selected from the group consisting of halogen; $C_1$-$C_2$-alkyl; $C_1$-$C_3$-haloalkyl; $C_1$-$C_2$-alkoxy; $C_1$-$C_3$-haloalkoxy; $C_1$-$C_2$-haloalkylthio; $SF_5$; cyano; nitro; hydroxy; or methylsulfonylamino; or is
(ii) 5- or 6 membered heteroaryl or heteroarylamino, which is each further unsubstituted or substituted by halogen, cyano, nitro, $C_1$-$C_4$-alkyl, $C_1$-$C_4$-haloalkyl, $C_1$-$C_4$-alkoxy, $C_1$-$C_4$-alkoxycarbonyl, $C_2$-$C_4$-alkanoyl, or phenyl or phenylsulfonyl which is each unsubstituted or substituted by halogen, cyano, nitro, methyl or methoxy; or is (iii) benzoyl or 5- or 6 membered heteroarylcarbonyl, which is each further unsubstituted or substituted by halogen, cyano, nitro, $C_1$-$C_4$-alkyl, $C_1$-$C_4$-haloalkyl, $C_1$-$C_4$-alkoxy, $C_1$-$C_4$-alkoxycarbonyl, $C_2$-$C_4$-alkanoyl or phenyl; or is
(iv) a $C_6$-$C_{12}$-bicarbocyclic radical; or is a
(v) a hetero-bicyclic ring radical comprising a total of 8 to 10 ring members, from which 1 to 5 members are same or different heteroatoms selected from the group consisting of B, N, O and S, and from which 0 to 2 members are a group —C(O)—, which bicyclic ring radical is further unsubstituted or substituted by halogen, cyano, hydroxyl, $C_1$-$C_4$-alkoxy, $C_1$-$C_4$-alkyl or $C_1$-$C_4$-haloalkyl; or is
(vi) a radical —$H_2C$—C(O)—NH—$R^4$, wherein $R^4$ is $C_1$-$C_4$-haloalkyl, $C_2$-$C_3$-alkynyl or cyano-$C_1$-$C_4$-alkyl; or
$R^0$ and Y together with the N-atom to which they are attached, form a piperidinyl or piperazinyl radical which is substituted by $C_1$-$C_4$-alkyl, $C_1$-$C_4$-alkoxy, unsubstituted or halogen-, $C_1$-$C_4$-alkyl-, $C_1$-$C_4$-haloalkyl-, amino- and/or $C_1$-$C_4$-alkoxy-substituted phenyl or benzoylamino, or unsubstituted or $C_1$-$C_4$-alkyl-, $C_1$-$C_4$-haloalkyl-, $C_3$-$C_6$-cycloalkyl- or halogen-substituted pyridyl or pyrimidinyl; subject to the proviso that at least one of A and Y must not be a phenyl radical if T is $CH_3$.

2. A compound according to claim 1, wherein
A is phenyl which is mono-substituted by chlorine, fluorine or $CF_3$,
Y is phenyl which is substituted by 2 or 3 same or different radicals selected from halogen or $CF_3$, and
T is $C_2$-$C_4$-alkyl, which is unsubstituted or substituted by halogen, cyclopropyl, cyclohexyl, trimethylsilyl, carboxy or $C_1$-$C_2$-alkoxycarbonyl; cyclopropyl or cyclohexyl; the radical of (+)- or (−)-camphor; phenyl which is unsubstituted or substituted by fluorine, chlorine, methyl, methoxy, $CF_3$ or nitro; or pyridyl, thienyl or pyrimidinyl; piperidinyl, piperazinyl, tetrahydropyranyl, morpholinyl, thiomorpholinyl or thiomorpholin-4-yl-1,1-dioxide, which is each unsubstituted or substituted by methyl.

3. A compound according to claim 1 of formula

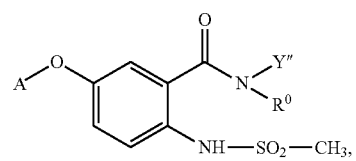

(Ic)

wherein
A is phenyl which is substituted as defined in claim 1;
$R^0$ is H or hydroxyl; and
Y″ is
(i) 5- or 6 membered heteroaryl or heteroarylamino, which is each further unsubstituted or substituted by halogen, cyano, nitro, $C_1$-$C_4$-alkyl, $C_1$-$C_4$-haloalkyl, $C_1$-$C_4$-alkoxy, $C_1$-$C_4$-alkoxycarbonyl, $C_1$-$C_4$-alkanoyl or phenyl or phenylsulfonyl which is each unsubstituted or substituted by halogen, cyano, nitro, methyl or methoxy; or is
(ii) benzoyl or 5- or 6 membered heteroarylcarbonyl, which is each further unsubstituted or substituted by halogen, cyano, nitro, $C_1$-$C_4$-alkyl, $C_1$-$C_4$-haloalkyl, $C_1$-$C_4$-alkoxy, $C_1$-$C_4$-alkoxycarbonyl, $C_1$-$C_4$-alkanoyl or phenyl; or is (iii) a $C_6$-$C_{12}$-bicarbocyclic radical; or is a (iv) a hetero-bicyclic ring radical comprising a total of 8 to 10 ring members, from which 1 to 5 members are same or different heteroatoms selected from the group consisting of B, N, O and S, and from which 0 to 2 are a group —C(O)—, which bicyclic ring radical is further unsubstituted or substituted by halogen, cyano, hydroxyl, $C_1$-$C_4$-alkoxy, $C_1$-$C_4$-alkyl or $C_1$-$C_4$-haloalkyl; or is (v) a radical —$H_2C$—C(O)—NH—$R^4$, wherein $R^4$ is $C_1$-$C_4$-haloalkyl, $C_2$-$C_3$-alkynyl or cyano-$C_1$-$C_4$-alkyl; or $R^0$ and Y together with the N-atom to which they are attached, form a piperidinyl or piperazinyl radical which is substituted by $C_1$-$C_4$-alkyl, $C_1$-$C_4$-alkoxy, unsubstituted or halogen-, $C_1$-$C_4$-alkyl-, halo-$C_1$-$C_4$-alkyl-, amino- and/or $C_1$-$C_4$-alkoxy-substituted phenyl or benzoylamino, or unsubstituted or $C_1$-$C_4$-alkyl-, $C_1$-$C_4$-haloalkyl-, $C_3$-$C_6$-cycloalkyl- or halogen-substituted pyridyl or pyrimidinyl.

4. A compound according to claim 3, wherein
A is phenyl which is mono-substituted by chlorine, fluorine or $CF_3$;
$R^0$ is H, and
Y" is (i) 2-, 3- or 4-pyridyl which is unsubstituted or substituted by halogen, $C_1$-$C_4$-alkyl or $C_1$-$C_2$-alkoxy; 2-thienyl which is unsubstituted or substituted by $C_1$-$C_2$-alkyl, $C_1$-$C_2$-alkoxycarbonyl; 2-thiazolyl which is unsubstituted or substituted by halogen, cyano, nitro, $C_1$-$C_2$-alkyl, $C_1$-$C_2$-haloalkyl, $C_1$-$C_2$-alkoxycarbonyl, or phenyl or phenylsulfonyl which is in turn each unsubstituted or substituted by halogen, cyano, nitro or methyl; 5-isothiazoyl which is unsubstituted or substituted by halogen or methyl; 2-oxazolyl, which is unsubstituted or substituted by $C_1$-$C_2$-alkyl or $C_1$-$C_2$-haloalkyl; or 1,3,4-thiadiazol-5-yl, which is unsubstituted or substituted by $C_1$-$C_2$-alkyl or $C_1$-$C_2$-haloalkyl; 2-, 3- or 4-pyridylamino, which is unsubstituted or substituted by halogen, $C_1$-$C_4$-alkyl or $C_1$-$C_2$-alkoxy; or (ii) benzoyl which is unsubstituted or substituted by halogen, or 2-, 3- or 4-pyridylcarbonyl which is unsubstituted or substituted by halogen or $C_1$-$C_4$-alkyl; or (iii) a radical

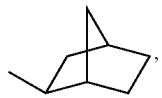

a radical

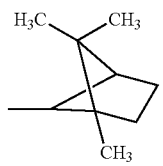

or indanyl; or (iv) benzothiazolyl, indolyl, quinolinyl, methylenedioxophenyl, benzooxaboronyl, triazolopyrimidinonyl or phthalhydrazidyl, which is each unsubstituted or substituted by halogen, $C_1$-$C_4$-alkyl, $C_1$-$C_2$-haloalkyl or hydroxy; or (v) a radical —$H_2C$—C(O)—NH—$CH_2$—C≡CH, —$H_2C$—C(O)—NH—$CH_2$—CN or —$H_2C$—C(O)—NH—$CH_2$—$CF_3$;

or $R^0$ and Y together with the N-atom to which they are attached, form a piperidinyl or piperazinyl radical, which is substituted by methyl; methoxy; halogen-, amino-, methoxy- or trifluoromethyl-substituted phenyl or benzoylamino; or halogen-, trifluoromethyl- and/or cyclopropyl-substituted pyridyl or pyrimidinyl.

5. A composition for the control of parasites, which contains as an active ingredient at least one compound of formula (I) according to claim 1, in addition to carriers and/or dispersants.

6. A method of controlling endoparasites, on warm-blooded animals, which comprises administering to the warm-blooded animals a veterinary effective amount of at least one compound of formula (I) according to claim 1.

7. A compound of the formula:

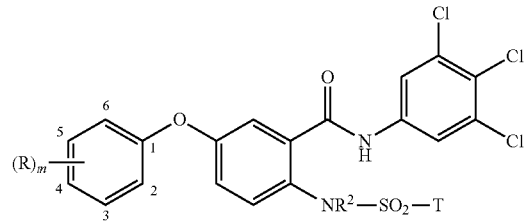

wherein
$(R)_m$ is H or 4-Cl;
T is 4-$CH_3$-phenyl, phenyl, 2-$NO_2$-4-$CF_3$-phenyl, 3-Cl-4-F-phenyl, 2-$CF_3$-4-F-phenyl, 4-$CF_3$-phenyl, 3,4-dimethoxyphenyl, 4-nitrophenyl, 4-chlorophenyl, 3,5-di-Cl-phenyl, 4-methoxyphenyl, 2-chloro-phenyl, 3-chloro-phenyl, 3-pyridyl, 3-methoxyphenyl, 3,4-dichlorophenyl, 2,6-dichlorophenyl, 2-methoxyphenyl, 2,4-dichlorophenyl, 2-$NO_2$-4-$OCH_3$-phenyl, 2,4-dimethoxyphenyl, ethyl, —$CH_2CF_3$, —$CH_2CH_2CF_3$, n-propyl, n-butyl, iso-butyl, —$CH_2CH_2Si(CH_3)_3$, cyclopropyl, cyclohexyl, 1-(benzyloxycarbonyl)-piperazin-4-yl, isopropyl, cyclohexylmethyl, (1R)-(--camphor, —$CH_2C(O)OC_2H_5$, —$CH_2C(O)OCH_3$, —$CH_2C(O)$OH, (1S)-(+)-campher, tetrahydro-2H-pyran-4-yl, —$N(CH_3)_2$, 1-methylpiperazin-4-yl, —$CH_2$—Cl,

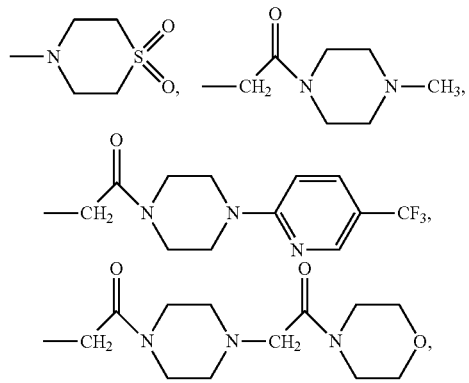

-continued

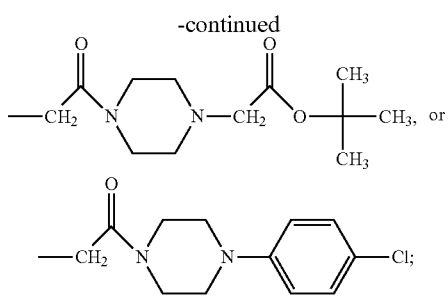

and
R² is H or —SO₂CH₂Cl.

8. A compound according to claim 7, wherein (R)$_m$ is 4-Cl and R² is H.

9. A compound according to claim 7, having the formula:

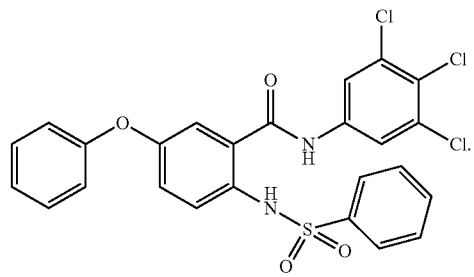 [SMILES: O=C(Nc1cc(Cl)c(Cl)c(Cl)c1)c1cc(Oc2ccccc2)ccc1NS(=O)(=O)c1ccccc1]

10. A composition for the control of parasites, which contains as an active ingredient the compound according to claim 7, in addition to carriers and/or dispersants.

11. A method of controlling endoparasites, on warm-blooded animals, which comprises administering to the warm-blooded animals a veterinary effective amount of the compound according to claim 7.

12. A compound of the formula:

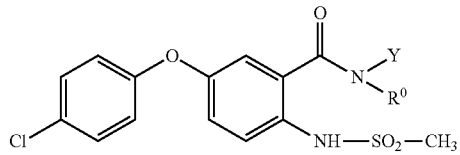

wherein
R⁰ is H or hydroxy; and
Y is

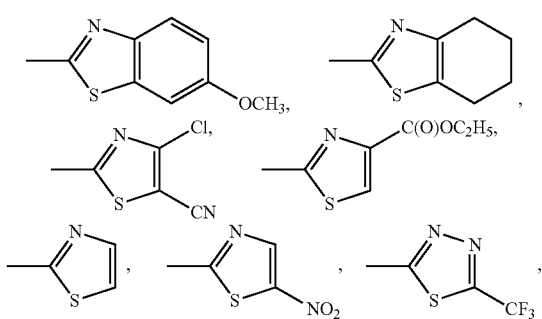

-continued

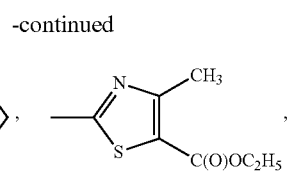

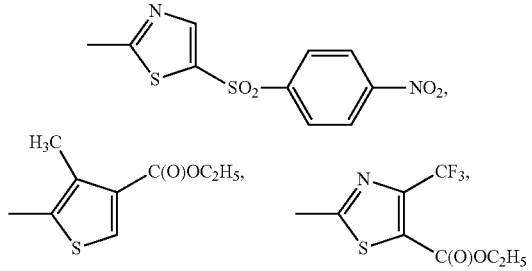

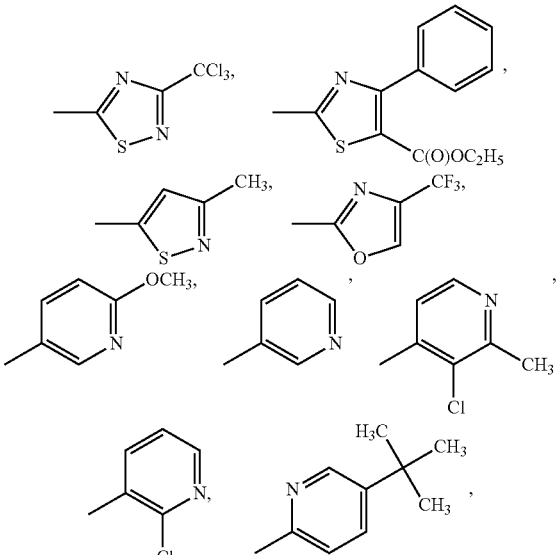

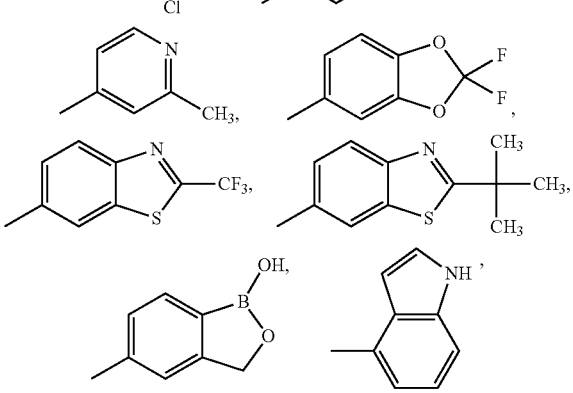

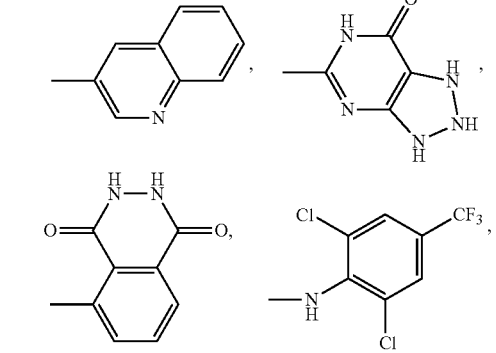

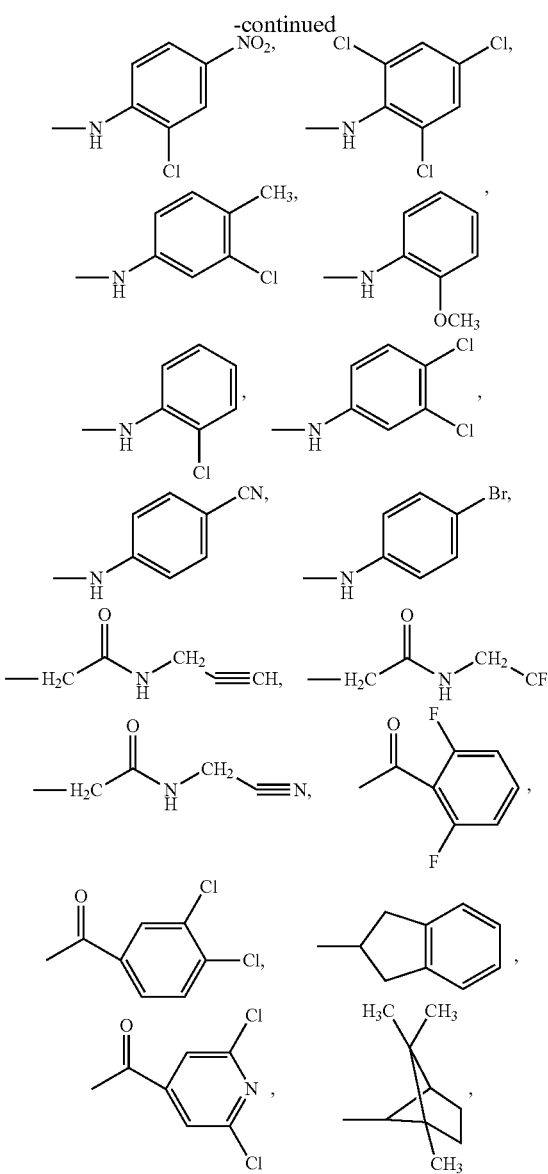

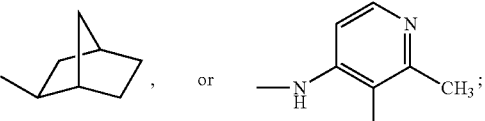

or $R^0$ and Y together with the N-atom to which they are attached, form

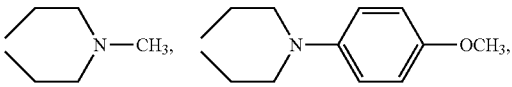

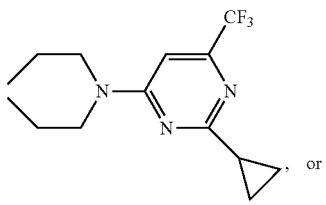

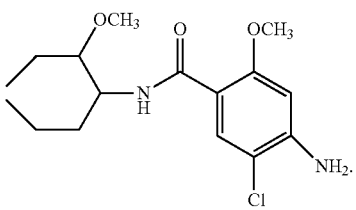

13. A compound according to claim 12, wherein $R^0$ is H.

14. A composition for the control of parasites, which contains as an active ingredient the compound according to claim 12, in addition to carriers and/or dispersants.

15. A method of controlling endoparasites, on warm-blooded animals, which comprises administering to the warm-blooded animals a veterinary effective amount of the compound according to claim 12.

* * * * *

UNITED STATES PATENT AND TRADEMARK OFFICE
CERTIFICATE OF CORRECTION

PATENT NO. : 10,047,040 B2
APPLICATION NO. : 15/502512
DATED : August 14, 2018
INVENTOR(S) : Gauvry et al.

Page 1 of 1

It is certified that error appears in the above-identified patent and that said Letters Patent is hereby corrected as shown below:

In the Claims

In Claim 1, Column 43, Line 30, delete "5- or 6 membered" and insert -- 5- or 6-membered --, therefor.

In Claim 1, Column 43, Line 61, delete "5- or 6 membered" and insert -- 5- or 6-membered --, therefor.

In Claim 1, Column 44, Line 1, delete "5- or 6 membered" and insert -- 5- or 6-membered --, therefor.

In Claim 1, Column 44, Line 6, after "is" delete "a".

In Claim 3, Column 44, Line 59, delete "5- or 6 membered" and insert -- 5- or 6-membered --, therefor.

In Claim 3, Column 44, Line 66, delete "5- or 6 membered" and insert -- 5- or 6-membered --, therefor.

In Claim 3, Column 45, Line 4, after "is" delete "a".

In Claim 7, Column 46, Line 47, delete "(1R)-(--campher," and insert -- (1R)-(-)-camphor, --, therefor.

In Claim 7, Column 46, Line 49, delete "(1S)-(+)-campher," and insert -- (1S)-(+)-camphor, --, therefor.

Signed and Sealed this
Ninth Day of April, 2019

Andrei Iancu
*Director of the United States Patent and Trademark Office*